US007335736B2

(12) United States Patent
Liu et al.

(10) Patent No.: US 7,335,736 B2
(45) Date of Patent: Feb. 26, 2008

(54) **COMPOSITIONS AND METHODS FOR DETECTING *TREPONEMA PALIDUM***

(75) Inventors: Hsi Liu, Tucker, GA (US); Bret M. Steiner, Chamblee, GA (US); Berta Rodes, Madrid (ES)

(73) Assignee: The United State of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/221,263

(22) Filed: Sep. 6, 2005

(65) Prior Publication Data

US 2006/0051823 A1 Mar. 9, 2006

Related U.S. Application Data

(60) Division of application No. 10/017,168, filed on Dec. 14, 2001, now Pat. No. 7,005,270, which is a continuation-in-part of application No. PCT/US00/16425, filed on Jun. 14, 2000.

(60) Provisional application No. 60/138,981, filed on Jun. 14, 1999.

(51) Int. Cl.
*C07K 1/00* (2006.01)
*A61K 39/00* (2006.01)
*A61K 39/02* (2006.01)

(52) U.S. Cl. ............... 530/350; 424/184.1; 424/191.1; 424/262.1; 424/265.1

(58) Field of Classification Search ............ 424/151.1, 424/184.1; 530/300, 324, 388.6
See application file for complete search history.

(56) References Cited

U.S. PATENT DOCUMENTS

| | | | |
|---|---|---|---|
| 4,738,932 A | 4/1988 | Yabusaki | |
| 4,894,328 A | 1/1990 | Alderete et al. | |
| 5,643,733 A | 7/1997 | Robinson et al. | |
| 5,643,751 A | 7/1997 | Robinson et al. | |
| 5,753,459 A | 5/1998 | Blanco et al. | |
| 5,770,719 A | 6/1998 | Kapoor et al. | |

FOREIGN PATENT DOCUMENTS

WO    WO 95/02186    1/1995

OTHER PUBLICATIONS

Thomas E. Creighton, in his book, "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph.*
Greenspan et al (Nature Biotechnology 7: 936-937, 1999).*
Bowie et al (Science, 1990, 257:1306-1310).*

Farshy et al., *Journal of Clinical Microbiology*, pp. 1109-1113 (Dec. '984).
Fraser et al., "Complete Genome Sequence of *Treponema pallidum*, the Syphilis Spirochete," *Science*, 281:375-388 (Jul. 17, 1998).
Green et al., "Identification, sequences, and expression of *Treponema pallidum* chemotaxis genes," *DNA Sequence*, 7(5):267-284 (1997) (Abstract Only).
Hook et al., *Journal of Clinical Microbiology*, pp. 241-244 (Aug. 1985).
Hunter et al., *Journal of Clinical Microbiology*, pp. 483-486 (Sep. 1982).
Norgard et al., *Journal of Clinical Microbiology*, pp. 711-717 (Oct. 1984).
Pillay et al., "Molecular Subtyping of *Treponema pallidum* Subspecies pallidum," *Sexually Trans. Dis.*, 25(8):408-414 (Sep. 1998).
Pillay et al., "Molecular Typing of *Treponema pallidum* in South Africa: Cross-Sectional Studies," *J. Clin. Microbio.*, 40(1):256-258 (Jan. 2002).
Seppa, "Researches solve syphilis genome.(genome of *Treponema pallidum* decoded)," *Science News*, www.findarticles.com/cf_0/m1200/n5_v154/21015212/print.jhtml, (Aug. 1, 1998).
Shevchenko et al., "Molecular Characterization and Cellular Localization of TpLRR, a Processed Leucine-Rich Repeat Protein of *Treponema pallidum*, the Syphilis Spirochete," *J. Bacter.*, 179(10):3188-3195 (May 1997).
Stamm et al., "Nucleotide Sequence of the *Treponema pallidum* Eno Gene," *DNA Sequence*, 7(5):261-265 (1997) (Abstract Only).
Stevens et al., *Journal of Clinical Microbiology*, pp. 191-195 (Feb. 1982).
Sutton et al., "Molecular Subtyping of *Treponema pallidum* in an Arizona County with Increasing Syphilis Morbidity: Use of Specimens from Ulcers and Blood," *J. Infect. Dis.*, 183:1601-1606 (Jun. 1, 2001).
Walfield et al., "Primary Structure of an Oligomeric Antigen of *Treponema pallidum*—For use in Sero-Diagnosis," *Infect. Immun.*, 57(2):633-635 (1989) (Abstract Only).
(No listed author) "Scientists Decipher Syphilis Genome," *Appl. Gen. News* (Sep. 1, 1998).
(No listed author) "Scientists Report on the Complete Genome of *Treponema pallidum*, The Syphilis Spirochete," *PR Newswire* (Jul. 16, 1998).

(Continued)

*Primary Examiner*—Nita Minnifield
*Assistant Examiner*—Vanessa L. Ford
(74) *Attorney, Agent, or Firm*—Klarquist Sparkman, LLP

(57) ABSTRACT

Methods for the specific and highly sensitive detection of *Treponema pallidum* infection comprising the use of specific antigenic proteins and peptides unique to *Treponema pallidum* are provided. In particular, detection assays based on recognition of acidic repeat protein are provided. The methods of the present invention are useful for detection of primary syphilis at early stages of infection. In addition, the methods and compositions disclosed herein are directed to the differential detection of specific *Treponema* infections enabling the identification of causative agents for specific *Treponema* disease states: syphilis (*Treponema pallidum* subspecies *pallidum*), yaws (*Treponema pallidum* subspecies *pertenue* CDC-1 or CDC-2 strain), and bejel (*Treponema pallidum* subspecies *endemicum*).

1 Claim, 17 Drawing Sheets

OTHER PUBLICATIONS

GenBank Accession No. AF015824, *Treponema pallidum* acidic repeat protein gene, complete cds. (Jan. 2, 1998).

GenBank Accession No. AF342806, *Treponema pallidum* subsp. pertenue strain CDC2 acidic repeat protein (arp) gene, complete cds. (Sep. 13, 2001).

GenBank Accession No. AF342807, *Treponema pallidum* subsp. endemicum strain Bosnia acidic repeat protein (arp) gene, complete cds. (Sep. 13, 2001).

GenBank accession No. AF411124, *Treponema pallidum* subsp. pallidum strain Nichols acidic repeat protein (arp) gene, complete cds. (Sep. 26, 2001).

GenBank Accession No. AF411126, *Treponema pallidum* subsp. pertenue strain CDC1 acidic repeat protein (arp) gene, complete cds. (Sep. 26, 2001).

* cited by examiner 1, 4 anti-*T. pallidum* serum
2, 3 anti-*arp* peptide Ab
5 pre-bled (rabbit)

GTCGATGCAC AGCTGACGCT CTCAGGTCTT GCACATATTG CGCGGCTGGT GCCGACATCT
CTCCTGCCAC CTGCTACAGT GTCAGGTTCA TCGGGGAATT GAGGAAACTG TTATCCGCGC
TCCCCATCTT CCGATACTGG ATCGGTGTCG GGGGGAGTAG GAGTGGGGAA GCGTCTGTGC
TGTATCGCGC TGGTGATGCG CGCGTTCTGG TACCTCAGTG CGAAGGGAGT CAGTATCGCT
TACGTGCCCG TTCATCGCAG TGGGGGCTCT CAAGATTCGA GCATGAGCAC AGCAGTGGGC
GATACGCTCC TTAACGCCTT CTTCGACGAG GGAATGGTGG TTACGGCAGT ACCGCCGGGT
GTACACGACG GCCAGACTAT AGCAGAAATT GCTGCATGTT TTGAAGTAAT GCCCGATTAC
GCGTTGTTGG TGCAGTTTCA TTCCGCTCGT CTCCCTGGTG GGGAAAGCCC TACCTCCCGT
GCCCGCGGCG CTTGGTCTTC AGAGAGGTTC CGTGCTGTGT GGACATTAGT GGATTTGCAT
ACGCAGCGCG CGTGTGTCTA TGCGTGTGTC GCCCCATACA GGGAGAGTAT TCCCGTTTCT
GAGTGTGTTG ACGTCGTTAC CCGTTGTATT GCGGAGCAGG CAATTTCGTA CATACGGGTG
GGCACGAGCA CCGATACAGC CGGAGTTCAG TTATAGAAAA TAGGGAATAC GTAAGGTGTC
TGCAGCGTCG CTTCAGCTGG GAGGAGTCTT ATGATTAAAC GCCACATGTT CGCAAAAAGG
GGTGTCAAAG GAAGATCTTA CCTGGTTAGG GTGAACACTG CGTTCTTAGT GCTTTGTGTT
GCTTCTGTCA CGCCGCTTTG GGCTGTGTGG GAAGGGAATG CAGAAATTGG CCCCCAGGGA
AGTTTTCTGC AGGACGGC (predicted start of arp) ATGTTTGTGCG CAGTGACATG TTCCCCAAAA ACACTGCTGT
TGAAATTAGC AACTTAGAAA AGAATGCCAA GGCTCAGGCA GTGGTTATTG GGCACGCAGG
GATCCCCGGT CTTCTAGTTA GCCTTGCACC CGCTGCTGCA GCACAGCTTG GGATTGGCGT
ATACCAAGCT GTGCGTGTAC GCGTACGTAC CTTGGGTACC GTGCGCGGTG GGTCTCAAAC
AAGTCAGGAC GGACTGTCCC TTGCATCTTT GCCGTCCCGT GTGCCTGCGC GCCCCGCGCA
GCGTGATCCT CTGTCATCCC CGCCGGCAGG TCACACTGTA CCGGAATATC GCGATACGGT
TATTTTCGAT GACCCGCGTT TGGTTTCCCC TTTGTCTCGT GAGGTGGAGG ACGCGCCGAA
GGTAGTGGAG CCGGCCTCTG AGCGTGAGGG AGGGGAGCGT GAGGTGGAGG ACGCGCCGAA
GGTAGTGGAG CCGGCCTCTG AGCGTGAGGG AGGGGAGCGT GAGGTGGAGG ACGTGCCGAA
GGTAGTGGAG CCGGCCTCTG AGCGTGAGGG AGGGGAGCGT GAGGTGGAGG ACGCGCCGAA
GGTAGTGGAG CCGGCCTCTG AGCGTGAGGG AGGGGAGCGT GAGGTGGAGG ACGTGCCGAA
GGTAGTGGAG CCGGCCTCTG AGCGTGAGGG AGGGGAGCGT GAGGTGGAGA ACGTGCCGAA
GGTAGTGGAG CCGGCCTCTG AGCGTGAGGG AGGGGAGCGT GAGGTGGAGG ACGCGCCGAA
GGTAGTGGAG CCGGCCTCTG AGCGTGAGGG AGGGGAGCGT GAGGTGGAGG ACGCGCCGAA
GGTAGTGGAG CCGGCCTCTG AGCGTGAGGG AGGGGAGCGT GAGGTGGAGG ACGTGCCGAA
GGTAGTGGAG CCGGCCTCTG AGCGTGAGGG AGGGGAGCGT GAGGTGGAGG ACGTGCCGAA
GGTAGTGGAG CCGGCCTCTG AGCGTGAGGG AGGGGAGCGT GAGGTGGAGG ACGTGCCGAA
GGTAGTGGAG CCGGCCTCTG AGCGTGAGGG AGGGGAGCGT GAGGTGGAGG ACGTGCCGAA
GGTAGTGGAG CCGGCCTCTG AGCGTGAGGG AGGGGAGCGT GAGGTGGAGG ACGTGCCGGG
GGTAGTGGAG CCGGCCTCTG GGCATGAAGG AGGGGAGCGT GAGGTGGAGG ACGTGCCGGG
GGTAGTGGAG CCGGCCTCTG GGCATGAAGG AGGGGAGCGT GAGGTCGCTT CTCAGCATAC
GAAGCAGCCA TCCCACTCGG TTTCCAACTC AGCTCCCAAT CAGTTTCGGA AACCCTGA
(end of arp)

GG GGGAACTCCC CTTTACGCTC CCTGACCTAT CCGAGTCAGA AATTGTGGTT CCGGAGGAAC
AGAAAGGACG TGCGCATCCC CAGGTGATAC CCGAGGGTGC GCCACGTGGA CTGCAACCTG
GTGAATACTA CGTACAGATT GCAGTCTTTC ATGACGCTAT CCAGGTGCAG AGCATTGTCC
ACCGTTACGG GGTAGAATAC CCCATCGCAG TGGAGCAGGA CATCCATGAA GGTAAGGTGC
GTTTCACCGT ATGCGTCGGT CCTGTCCAAA AAGACGAACG CGGCGCGGTA CTAGAGAACT
TCCAAAGGTT TGGATTCAAG GACGCCTTTC TGAAAAAGGC GCGATGATCA GGTCGGCCCT
CCTCTTCCCC TCGTGACCGT GGTGACTCGC CCCGAAGGGG GCGCACAGAG CCCGAAGGAA
CGGAAGGGAA GGGGCAGACT TAACTATTTC TTTGTTTTTT TGAGCACGTA AAACGGCGCC
ATCTCCTTTG AAGGCTTTCC TGCGCCGGGA GCGCCCATGT AGCGAACGGA GTTACTGTCT
ATCAGCTCGT ACAGCTCTTT CTCGTGCGGT GCCTTCGATT GCTCCGAGGA CACAAGCGAG
AGTTCGACAA TTCCGTCTTC ACGTACCATC CACGTACCGC GATACGTAAG AGGAGAAGGT
GCCGACTTCT TCTCAAGGGC AAGCTCTACC TTTTGCGCAG TGCCATCCGC GTTGAACGTC ACAGTC

FIGURE 5

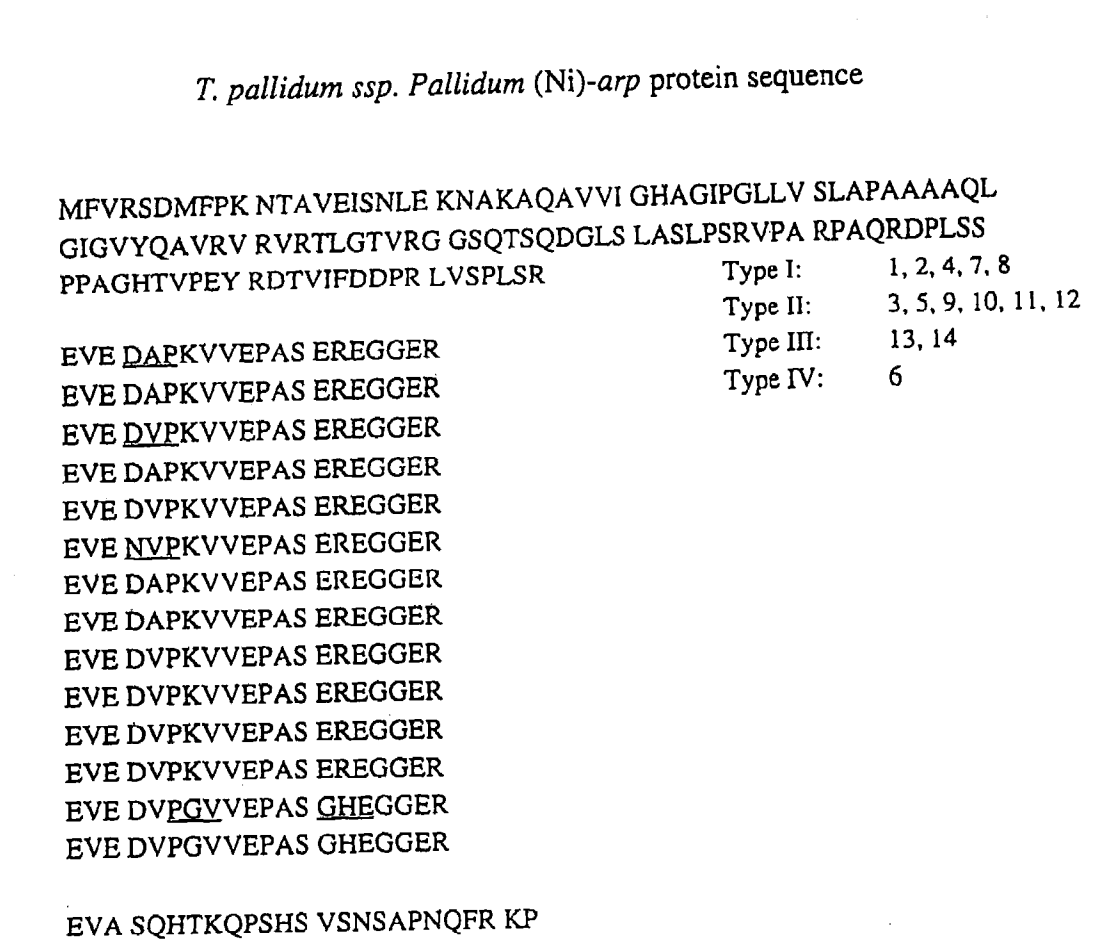

*T. pallidum ssp. Pallidum* (Ni)-*arp* protein sequence

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLSR

| | |
|---|---|
| Type I: | 1, 2, 4, 7, 8 |
| Type II: | 3, 5, 9, 10, 11, 12 |
| Type III: | 13, 14 |
| Type IV: | 6 |

EVE DAPKVVEPAS EREGGER
EVE DAPKVVEPAS EREGGER
EVE DVPKVVEPAS EREGGER
EVE DAPKVVEPAS EREGGER
EVE DVPKVVEPAS EREGGER
EVE NVPKVVEPAS EREGGER
EVE DAPKVVEPAS EREGGER
EVE DAPKVVEPAS EREGGER
EVE DVPKVVEPAS EREGGER
EVE DVPKVVEPAS EREGGER
EVE DVPKVVEPAS EREGGER
EVE DVPKVVEPAS EREGGER
EVE DVPGVVEPAS GHEGGER
EVE DVPGVVEPAS GHEGGER

EVA SQHTKQPSHS VSNSAPNQFR KP

FIGURE 6

*T. pallidum ssp. Pertenue* (CDC-2) nucleotide sequence

| | | | | |
|---|---|---|---|---|
| ATGTTTGTGC | GCAGTGACAT | GTTCCCCAAA | AACACTGCTG | TTGAAATTAG |
| CAACTTAGAA | AAGAATGCCA | AGGCTCAGGC | AGTGGTTATT | GGGCACGCAG |
| GGATCCCCGG | TCTTCTAGTT | AGCCTTGCAC | CCGCTGCTGC | AGCACAGCTT |
| GGGATTGGCG | TATACCAAGC | TGTGCGTGTA | CGCGTACGTA | CCTTGGGTAC |
| CGTGCGCGGT | GGGTCTCAAA | CAAGTCAGGA | CGGACTGTCC | CTTGCATCTT |
| TGCCGTCCCG | TGTGCCTGCG | CGCCCCGCGC | AGCGTGATCC | TCTGTCATCC |
| CCGCCGGCAG | GTCACACTGT | ACCGGAATAT | CGCGATACGG | TTATTTTCGA |
| TGACCCGCGT | TTGGTTTCCC | CTTTGTCTCG | TGAGGTGGAG | GACGTGCCGA |
| AGGTAGTGGA | GCCGGCCTCT | GAGCGTGAGG | GAGGGGAGCG | TGAGGTGGAG |
| GACGTGCCGA | AGGTAGTGGA | GCCGGCCTCT | GAGCGTGAGG | GAGGGGAGCG |
| TGAGGTGGAG | GACGTGCCGA | AGGTAGTGGA | GCCGGCCTCT | GAGCGTGAGG |
| GAGGGGAGCG | TGAGGTGGAG | GACGTGCCGA | AGGTAGTGGA | GCCGGCCTCT |
| GAGCGTGAGG | GAGGGGAGCG | TGAGGTGCGT | TCTCAGCATA | CGAAGCAGCC |
| ATCCCACTCG | GTTCCAACT | CAGCTCCCAA | TCAGTTTCGG | AAACCCTGA |

FIGURE 7

*T. pallidum ssp. Pertenue* (CDC-2) *arp* protein sequence

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLSR

EVE DVPKVVEPAS EREGGER
EVE DVPKVVEPAS EREGGER
EVE DVPKVVEPAS EREGGER
EVE DVPKVVEPAS EREGGER

EVA SQHTKQPSHS VSNSAPNQFR KP

FIGURE 8

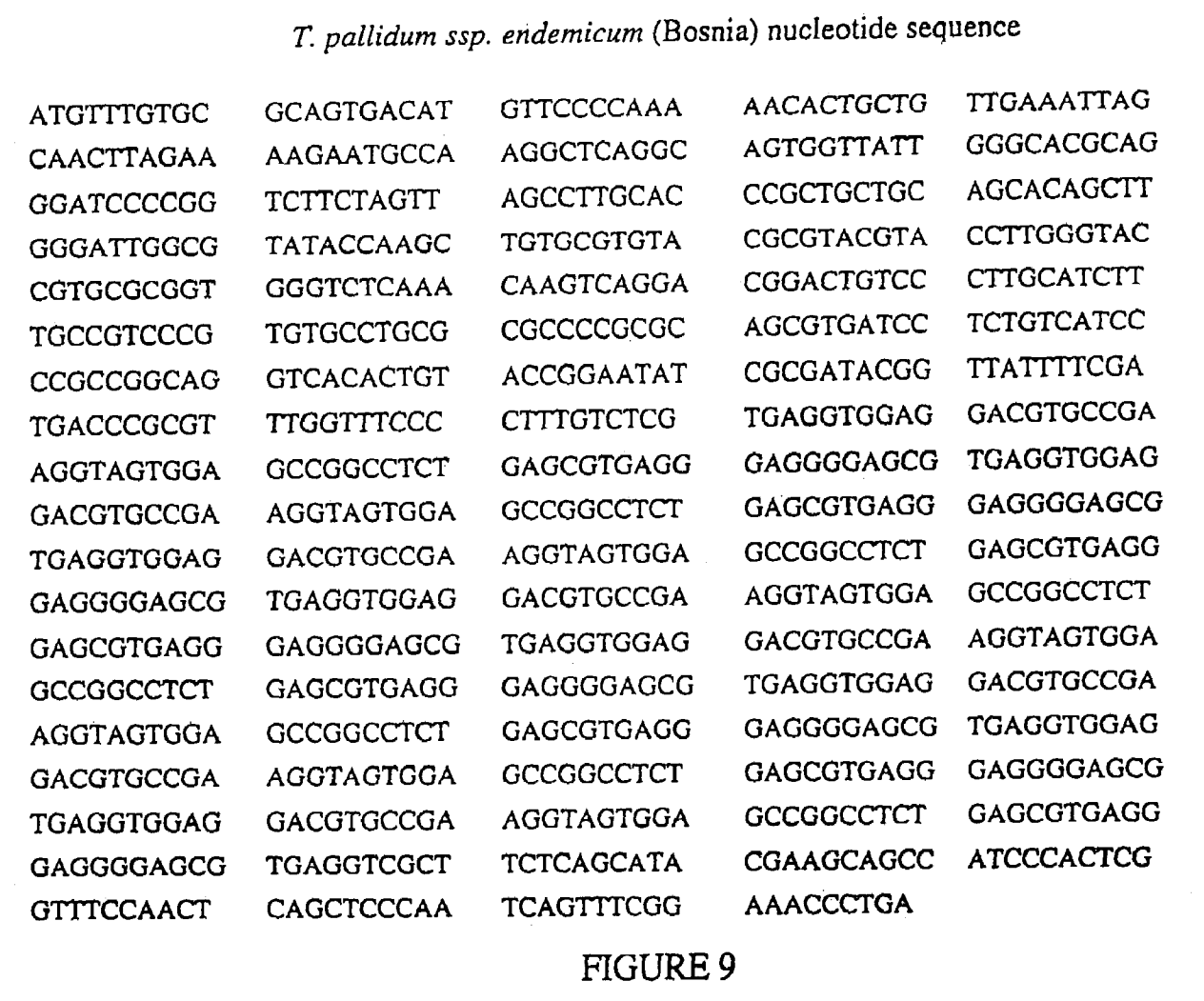

*T. pallidum ssp. endemicum* (Bosnia) nucleotide sequence

| | | | | |
|---|---|---|---|---|
| ATGT

*T. pallidum ssp. endemicum* (Bosnia) *arp* protein sequence

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLSR

EVE DVPKVVEPAS EREGGER
EVE DVPKVVEPAS EREGGER
EVE DVPKVVEPAS EREGGER
EVE DVPKVVEPAS EREGGER
EVE DVPKVVEPAS EREGGER
EVE DVPKVVEPAS EREGGER
EVE DVPKVVEPAS EREGGER
EVE DVPKVVEPAS EREGGER

EVA SQHTKQPSHS VSNSAPNQFR KP

FIGURE 10 arp #1
SEQ ID NO: 7          LVSPL REVEDAPKVVEPASarp #2
SEQ ID NO: 8          -SR-EVED APKVVEPASEREGGarp #3
SEQ ID NO: 9          -PK VVEPASEREGGEREVEDA- TP-arp #4
SEQ ID NO: 10         PKNTAVEISNLE KNAKAQAVV TP-arp #5
SEQ ID NO: 11         GHAGIPGLLV SLAPAAAAQLGIGVY TP-arp #6
SEQ ID NO: 12         VPA RPAQRDPLSS PPAGHTVPEY RD TP-arp #7
SEQ ID NO: 13         VVEPAS EREGGEREVE DVPKV TP-arp #8
SEQ ID NO: 14         VVEPASGHEGGEREVA SQHT KQPSHS TP-arp #9
SEQ ID NO: 15         EVEDVPKVVEPASEREGGER TP-arp #10
SEQ ID NO: 16         EVENVPKVVEPASEREGGER TP-arp #11
SEQ ID NO: 17         EVEDAPKVVEPASEREGGER TP-arp #12
SEQ ID NO: 18         EVEDVPGVVEPASGHEGGER

*T. pallidum* subspecies. *pallidum*, Nichols strain

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLS

| | |
|---|---|
| REVEDAPKVVEPASEREGGE | Type I: 1, 2, 4, 7, 8 |
| REVEDAPKVVEPASEREGGE | Type II: 3, 5, 6,9, 10, 11, 12 |
| REVEDVPKVVEPASEREGGE | Type III: 13, 14 |
| REVEDAPKVVEPASEREGGE | |
| REVEDVPKVVEPASEREGGE | |
| REVEDVPKVVEPASEREGGE | |
| REVEDAPKVVEPASEREGGE | |
| REVEDAPKVVEPASEREGGE | |
| REVEDVPKVVEPASEREGGE | |
| REVEDVPKVVEPASEREGGE | |
| REVEDVPKVVEPASEREGGE | |
| REVEDVPKVVEPASEREGGE | |
| REVEDVPGVVEPASGHEGGE | |
| REVEDVPGVVEPASGHEGGE | |

REVA SQHTKQPSHS
VSNSAPNQFRNPEGELPFTLPDLSESEIVVPEEQKGRAHP
QVIPEGAPRG LQPGEYYVQI AVFHDAIQVQ SIVHRYGVEYPIAVEQDIHE
GKVRFTVCVG PVQKDERGAV
LENFQRFGFK DAFLKKAR

FIG. 15

*T. pallidum* subspecies *pertenue*, CDC-2 strain

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLS

REVEDVPKVVEPASEREGGE
REVEDVPKVVEPASEREGGE
REVEDVPKVVEPASEREGGE
REVEDVPKVVEPASEREGGE

REVA SQHTKQPSHS VSNSAPNQFR NPEGELPFTL PDLSESEIVV
PEEQKGRAHP QVIPEGAPRG LQPGEYYVQI AVFHDAIQVQ SIVHRYGVEY
PIAVEQDIHE GKVRFTVCVG PVQKDERGAV LENFQRFGFK DAFLKKAR

FIG. 16

*T. pallidum* subspecies *endemicum*, Bosnia strain

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLS

REVEDVPKVVEPASEREGGE
REVEDVPKVVEPASEREGGE
REVEDVPKVVEPASEREGGE
REVEDVPKVVEPASEREGGE
REVEDVPKVVEPASEREGGE
REVEDVPKVVEPASEREGGE
REVEDVPKVVEPASEREGGE
REVEDVPKVVEPASEREGGE

REVA SQHTKQPSHSVSNSAPNQFR NPEGELPFTL PDLSESEIVV
PEEQKGRAHP
QVIPEGAPRGLQPGEYYVQI AVFHDAIQVQ SIVHRYGVEY PIAVEQDIHE
GKVRFTVCVGPVQKDERGAV LENFQRFGFK DAFLKKAR

FIG. 17

*T. pallidum* subspecies. *pertenue*, CDC-1 strain

MFVRSDMFPK NTAVEISNLE KNAKAQAVVI GHAGIPGLLV SLAPAAAAQL
GIGVYQAVRV RVRTLGTVRG GSQTSQDGLS LASLPSRVPA RPAQRDPLSS
PPAGHTVPEY RDTVIFDDPR LVSPLSREGGE

REVEDVPKVVEPASEREGGE
REVEDVPKVVEPASEREGGE
REVEDVPKVVEPASEREGGE
REVEDVPKVVEPASEREGGE
REVEDVPKVVEPASEREGGE
REVEDVPKVVEPASEREGGE

REVASQHTK QPSHSVSNSA PNQFRNPEGE LPFTLPDLSE SEIVVPEEQK
GRAHPQVIPE GAPRGLQPGE YYVQIAVFHD AIQVQSIVHR YGVEYPIAVE
QDIHEGKVRF TVCVGPVQKD ERGAVLENFQ RFGFKDAFLK KAR

COMPOSITIONS AND METHODS FOR DETECTING *TREPONEMA PALIDUM*

CROSS REFERENCE TO RELATED APPLICATIONS

This is a divisional application of U.S. application Ser. No. 10/017,168, filed Dec. 14, 2001, now U.S. Pat. No. 7,005,270, which is a continuation-in-part application of PCT International Application US00/16425, filed Jun. 14, 2000, which claims the benefit of U.S. Provisional Application 60/138,981, filed Jun. 14, 1999; each of the foregoing applications is incorporated in its entirety herein by reference.

STATEMENT OF GOVERNMENT SUPPORT

This invention was made by the Centers for Disease Control and Prevention, an agency of the United States Government. Therefore, the United States Government has certain rights in this invention.

FIELD OF THE DISCLOSURE

The present disclosure relates to the fields of microbiology and immunology and more specifically relates to compositions and methods for diagnosing diseases caused by *Treponema pallidum* such as syphilis. In particular, the disclosure pertains to the detection of specific antigenic proteins and peptides that are unique to *Treponema pallidum*.

BACKGROUND OF THE DISCLOSURE

*Treponema pallidum* (*T. pallidum*) is the microaerophilic spirochete that causes syphilis, a systemic venereal disease with multiple clinical presentations. Other closely related treponemes cause pinta (*Treponema carateum*), yaws (*Treponema pallidum* subspecies *pertenue*), and bejel (*Treponema pallidum* subspecies *endemicum*).

In 1996 over 11,000 cases of primary and secondary syphilis in the United States were reported to the U.S. Centers for Disease Control and Prevention. The initial infection causes an ulcer at the site of infection; however, the bacteria move throughout the body, damaging many organs over time. Although treatment with penicillin in the early stages may be successful, the early symptoms of syphilis can be very mild, and many people do not seek treatment when they first become infected. This delay in seeking treatment is harmful because the damage to the organs in late syphilis cannot be reversed. Also of increasing concern is the risk of transmitting and acquiring the human immunodeficiency virus (HIV) that causes AIDS via open ulcers caused by syphilis.

Medical experts describe the course of the syphilis disease by dividing it into stages: primary, secondary, latent, and tertiary (late). An infected person who has not been treated may infect others during the first two stages, which usually last one to two years. The bacteria spread from the initial ulcer of an infected person to the skin or mucous membranes of the genital area, the mouth, or the anus of a sexual partner. The bacteria can also pass through broken skin on other parts of the body. In its late stages, untreated syphilis, although not contagious, can cause serious heart abnormalities, mental disorders, blindness, other neurologic problems, and even death.

The first symptom of primary syphilis is an ulcer called a chancre. The chancre can appear within 10 days to three months after exposure, but it generally appears within two to six weeks. The chancre is usually found on the part of the body exposed to the partner's ulcer, such as the penis, the vulva, or the vagina. A chancre also can develop on the cervix, tongue, lips, or other parts of the body. Because the chancre may be painless and may occur inside the body, it may go unnoticed. Although the chancre disappears within a few weeks whether or not a person is treated, if the infection is not treated during the primary stage, about one-third of those infected will progress to the chronic stages of syphilis.

Secondary syphilis is often marked by a skin rash that is characterized by brown sores about the size of a penny. The rash appears anywhere from three to six weeks after the chancre appears. While the rash may cover the whole body, the palms of the hands and soles of the feet are the most common sites of presentation. Because active bacteria are present in these sores, any physical contact, sexual or nonsexual, with the broken skin of an infected person may spread the infection at this stage. The rash usually heals within several weeks or months. Other symptoms may also occur such as mild fever, fatigue, headache, sore throat, patchy hair loss, and swollen lymph glands throughout the body. These symptoms may be very mild and, like the chancre of primary syphilis, will disappear without treatment.

The signs of secondary syphilis may come and go over the next one to two years. If untreated, syphilis may lapse into a latent stage during which the disease is no longer contagious and no symptoms are present. Although many individuals who are not treated will suffer no further consequences of the disease, approximately one-third of those who have secondary syphilis develop the complications of late, or tertiary, syphilis.

In the tertiary stage of syphilis, bacteria damage the heart, eyes, brain, nervous system, bones, joints, or almost any other part of the body. This stage can last for years, or even decades. Late syphilis can result in mental illness, blindness, other neurologic problems, heart disease, and even death.

During the early stages of infection, syphilis bacteria also frequently invade the nervous system, and approximately three to seven percent of persons with untreated syphilis develop neurosyphilis. However, development of neurosyphilis can take up to twenty years and some persons with neurosyphilis never develop any symptoms. Those who do present symptoms may experience headaches, stiff necks, and fever, which result from an inflammation of the lining of the brain. Seizures and symptoms of stroke such as numbness, weakness, or visual problems may also afflict those patients with neurosyphilis. Although neurosyphilis can be treated, treatment may be more difficult and its course may be different in persons infected with HIV.

The effects of syphilis in pregnant women are particularly compelling because of the consequential effects on the unborn child. It is likely that an untreated pregnant woman with active syphilis will pass the infection to her unborn child. About 25 percent of these pregnancies result in stillbirth or neonatal death. Between 40 to 70 percent of such pregnancies will yield a syphilis-infected infant. Some infants with congenital syphilis may have symptoms at birth, but most develop symptoms between two and three weeks post partum. These symptoms may include skin sores, rashes, fever, swollen liver and spleen, jaundice, anemia, and various deformities. Care must be taken in handling an infant with congenital syphilis because the moist sores are infectious. Rarely, the symptoms of syphilis go undetected in infants. As infected infants become older children and teenagers, they may develop the symptoms of late-stage syphilis including bone, tooth, eye, ear, and brain damage.

Due to the sometimes serious and life threatening effects of syphilis infection, and the risk of transmitting or contracting HIV, specific and early diagnosis of the infection is essential. Syphilis, however, has sometimes been called "the great imitator" because its early symptoms are similar to those of many other diseases. Therefore, a doctor usually does not rely upon recognition of the signs and symptoms of syphilis, but performs both microscopic identification of syphilis bacteria and blood tests.

To diagnose syphilis by a microscopic identification of the bacterium, the physician may take a scraping from the surface of the ulcer or chancre and examine it under a special "dark-field" microscope to detect the organism. However, dark-field microscopy requires considerable skill and is prone to misinterpretation. For these reasons, most cases of syphilis are diagnosed serologically. The blood tests most often used to detect evidence of syphilis are the VDRL (Venereal Disease Research Laboratory) test and the RPR (rapid plasma reagent) test. These non-treponemal tests employ natural lipids, cardiolipin and lecithin, to detect antibodies against non-specific antigens during an active syphilitic infection.

However, one of the complaints about the non-treponemal tests is their lack of specificity in comparison to the treponemal tests. Due to the occurrence of false positives and false negatives when using non-treponemal tests, more than one blood test is usually required. The rate of false positives and the need for multiple blood tests is increased in those individuals with autoimmune disorders, certain viral infections, and other conditions involving substantial tissue destruction or liver involvement. Although treponemal-based tests such as the fluorescent treponemal antibody-absorption (FTA-ABS) and the *T. pallidum* hemagglutination assay (TPHA) may be used to confirm a positive test result, treponemal-based tests are more expensive and more difficult to use than non-treponemal tests. Treponemal tests also cannot be used as tests for cure after treatment because they remain positive even after eradication of the infection.

Some treponemal tests currently in use depend upon the detection of proteins anchored in the *T. pallidum* cytoplasmic membrane. Detection of such proteins is particularly difficult because of the unusual structure of the *T. pallidum* membrane, which consists predominantly of lipids that tend to "shield" these proteins from detection. This shielding effect often delays the host's immune response frequently resulting in false negative serological results.

Currently available treponemal tests depend mainly on the detection of antibodies to cytoplasmic membrane anchored lipoproteins. Response to these proteins is typically delayed because of their lack of surface exposure since the outer membrane consists mainly of lipids and is protein poor. The tests often yield confusing and inaccurate results because these lipoproteins are highly antigenic and may be responsible for the long lasting response in treponemal tests. Because of this latter property, treponemal tests cannot differentiate a current versus a past infection.

Syphilis usually is treated with penicillin, administered by injection. Other antibiotics are used for treating patients allergic to penicillin. A patient typically loses the ability to transmit syphilis within 24 hours from initiating therapy. Some infected individuals, however, do not respond to the usual doses of penicillin. Therefore, it is important that patients undergoing treatment for syphilis are monitored through periodic blood tests to ensure that the infectious agent has been completely destroyed. Persons with neurosyphilis may need to be re-tested for up to two years after treatment.

In all stages of syphilis, proper treatment may cure the disease, but in late syphilis, damage already done to body organs cannot be reversed. Screening and treatment of infected individuals, or secondary prevention, is one of the few options available for preventing the advanced stages of syphilis disease. Testing and treatment early in pregnancy is the best way to prevent syphilis in infants and should be a routine part of prenatal care. A vital component in the successful treatment and prevention of syphilis is early and accurate detection of *T. pallidum* infection.

Diseases Associated with other Treponemal Infections

Pinta, caused by *Treponema carateum*, has become very rare, and is limited to the warm arid tropical Americas (in particular, Mexico, Central America, and Colombia). The disease manifests in the form of primary and secondary lesions. The primary lesions, which may persist for several years, are coalescing pruritic papules on the extremities, face, neck, chest, or abdomen. The secondary lesions are disseminated small, scaly papules, called pintids. These may become dyschromic (i.e., change from the normal color of the skin). Late lesions are achromic (without pigment).

Bejel, caused by *Treponema pallidum* subspecies *endemicum*, is known by many names in local languages as a form of syphilis that is not sexually transmitted and occurs in children. Transmission can be by direct contact, and also (in contradistinction to all the other treponemal diseases) via fomites, as in sharing drinking vessels and eating utensils. Except for the fact that the primary lesion, which is probably in the oral mucosa, is rarely observed, the disease is virtually identical to syphilis, with gummas, condylomata lata, and periostitis.

Yaws, caused by *Treponema pallidum* subspecies *pertenue*, occurs in warm, humid tropics. Yaws disease also predominantly manifests in the form of lesions. The primary lesion is a papillomatous skin lesion that heals spontaneously, only to be followed by the secondary lesions, which are large papillomatous nodules that are widely distributed over the skin surface. The late stage of the disease is characterized by gummas of various bones and the nasopharynx as well as destruction lesions of the skin, lymph nodes, and bones. The skin over the gummas may ulcerate. The disease is present in primitive tropical areas in parts of South America, Central Africa, and Southeast Asia and is spread by direct contact with infected skin.

Though some treatments for treponemal infection are available, control of treponemal diseases is managed by eliminating person to person spread. Accordingly, early detection of treponemal infection is vital for reducing widespread dissemination of related diseases.

Thus, there remains a need for accurate and improved methods and compositions for the effective, accurate early diagnosis of *T. pallidum* infection and methods for monitoring *T. pallidum* therapy.

SUMMARY OF THE DISCLOSURE

Efficient and sensitive methods and compositions for the detection of *Treponema* infection are disclosed. In particular, methods and compositions for the detection of *Treponema pallidum* (*T. pallidum*) are disclosed. In accordance with certain of these methods, a sample is analyzed for the presence of protein products of particular genes such as the acidic repeat protein (arp) gene. Specific embodiment methods for detecting *T. pallidum* are based on the detection of certain peptides, and/or secreted acidic repeat protein gene products and antibodies against these protein/peptides in infected individuals are disclosed.

In addition, methods are disclosed wherein samples are combined with antibodies specific for *T. pallidum* antigens, such as immunogenic proteins, under conditions to form an antibody-antigen complex. More particularly, methods are disclosed wherein samples are combined with proteins or peptides of the arp gene. Detection of antibodies indicates the presence of *T. pallidum* in a patient.

In one embodiment, assays comprising methods for the detection of various gene products of the antigenic sequences are provided.

In another embodiment, methods specific for the detection of the arp gene, acidic repeat protein, are provided.

In an additional embodiment, methods and compositions are provided for the differential diagnosis of treponemal infection. In particular, methods that enable the specific identification of *Treponema pallidum* subspecies *pallidum*, *Treponema pallidum* subspecies *pertenue*, CDC-1 strain, *Treponema pallidum* subspecies *pertenue*, CDC-2 strain, and *Treponema pallidum* subspecies *endemicum* are provided.

Accordingly, certain methods described herein provide a sensitive assay for the detection of *T. pallidum*.

Also provided is an assay capable of detecting proteins comprising antigenic gene products of *T. pallidum*.

Methods described herein can be used for early detection of primary syphilis.

Further embodiments include methods and compositions for differential diagnosis of syphilis, yaws, and bejel.

Also provided are antibodies specific for *T. pallidum*.

A further embodiment is a kit for automated point-of-use analysis for detecting *T. pallidum* in biological samples.

In a further embodiment, this disclosure provides a method for early detection of *T. pallidum* that is independent of antigenic proteins wholly contained in the cytoplasmic membrane of the infectious agent.

Yet another embodiment is a method for treating *T. pallidum* infection comprising the use of antibodies raised against antigenic gene products of *T. pallidum*.

An additional embodiment is an immunoassay for the detection of antigenic gene products of *T. pallidum*.

Another embodiment is a method for detecting acidic repeat protein.

Yet other embodiments provides immunoassays for the detection of syphilis, yaws or bejel using acidic repeat protein and/or peptides derived thereof, a solid phase particle that may be used in rapid-flow cytometry-type diagnosis of *T. pallidum*, and a solid phase particle that may be used in agglutination-type assay for a rapid diagnosis of *T. pallidum* infection.

Also provided are methods for detecting *T. pallidum* comprising enzymatic amplification (ELISA).

The present disclosure also provides an assay capable of detecting antibodies to *T. pallidum*.

Another embodiment is a kit for automated point-of-use analysis for detecting anti-*T. pallidum* antibodies in biological samples.

The disclosure also provides an immunoassay for the detection of antibodies against *T. pallidum*.

Further methods are specifically for the detection of antibodies to acidic repeat protein. Specific examples of such methods include an immunoassay for the detection of antibodies to acidic repeat protein in people infected with syphilis, yaws, or bejel using acidic repeat protein and/or peptides derived therefrom.

Another embodiment is a solid phase particle that may be used in rapid-flow cytometry type of diagnosis of *T. pallidum* infection using the arp protein or peptides.

Also provided is a method for detecting anti-*T. pallidum* antibodies comprising enzymatic amplification (ELISA).

These and other features and advantages will become apparent after a review of the following detailed description of the disclosed embodiments and the appended claims.

BRIEF DESCRIPTION OF THE FIGURES

FIG. 5 provides the nucleotide sequence for *Treponema pallidum* arp (SEQ ID NO: 1).

FIG. 6 provides the amino acid sequence for *T. pallidum* subspecies *pallidum* arp (SEQ ID NO: 2) and indicates the various types of repeats observed in the protein.

FIG. 7 provides the nucleotide sequence for *T. pallidum* ssp. *Pertenue* (CDC-2) (SEQ ID NO: 3).

FIG. 8 provides the amino acid sequence for *T. pallidum* subspecies *pertenue*, CDC-2 strain arp (SEQ ID NO: 4) and indicates the various types of repeats observed in the protein.

FIG. 9 provides the nucleotide sequence for *T. pallidum* ssp. *endemicum* (Bosnia) (SEQ ID NO: 5).

FIG. 10 provides the amino acid sequence listing for *T. pallidum* subspecies *endemicum*, Bosnia strain arp (SEQ ID NO: 6) and indicates the various types of repeats observed in the protein.

FIG. 11 provides the protein sequences for example arp repeat peptides of the present disclosure.

FIG. 14 provides the complete amino acid sequence for *T. pallidum* subspecies *pallidum* Nichols strain arp (SEQ ID NO: 20) and indicates the various types of repeats observed in the protein.

FIG. 15 provides the complete amino acid sequence for *T. pallidum* subspecies *pertenue*, CDC-2 strain arp (SEQ ID NO: 22) and indicates the various types of repeats observed in the protein.

FIG. 16 provides the complete amino acid sequence for *T. pallidum* subspecies *endemicum*, Bosnia strain arp (SEQ ID NO: 24) and indicates the various types of repeats observed in the protein FIG. 17 provides the complete amino acid sequence for *T. pallidum* subspecies *pertenue*, CDC-1 strain arp (SEQ ID NO: 26) and indicates the various types of repeats observed in the protein.

SEQUENCE LISTING

The nucleic and amino acid sequences listed in the accompanying sequence listing are shown using standard letter abbreviations for nucleotide bases, and single letter code for amino acids, as defined in 37 C.F.R. § 1.822. Only one strand of each nucleic acid sequence is shown, but the complementary strand is understood as included by any reference in the displayed strand. In the accompanying sequence listing:

SEQ ID NO: 1 shows the nucleic acid sequence (GenBank Accession No. AF015824) of the acidic repeat protein (arp) gene of *T. pallidum* subspecies *pallidum*, Nichols strain.

SEQ ID NO: 2 shows the amino acid sequence of the protein encoded by the acidic repeat protein (arp) gene of *T. pallidum* subspecies *pallidum*, Nichols strain.

SEQ ID NO: 3 shows the nucleic acid sequence of the acidic repeat protein (arp) gene of *T. pallidum* subspecies *pertenue*, CDC-2 strain.

SEQ ID NO: 4 shows the complete amino acid sequence for the acidic repeat protein (arp) gene of *T. pallidum* subspecies *pertenue*, CDC-2 strain.

SEQ ID NO: 5 shows the nucleic acid sequence of the acidic repeat protein (arp) gene of *T. pallidum* subspecies *endemicum*, Bosnia strain.

SEQ ID NO: 6 shows the complete amino acid sequence for the acidic repeat protein (arp) gene of *T. pallidum* subspecies *endemicum*, Bosnia strain.

SEQ ID NO: 7 shows the amino acid sequence of a peptide isolated from the acidic repeat protein.

SEQ ID NO: 8 shows the amino acid sequence of a peptide isolated from the acidic repeat protein.

SEQ ID NO: 9 shows the amino acid sequence of a peptide, arp 3, isolated from the acidic repeat protein.

SEQ ID NO: 10 shows the amino acid sequence of a peptide isolated from the acidic repeat protein.

SEQ ID NO: 11 shows the amino acid sequence of a peptide isolated from the acidic repeat protein.

SEQ ID NO: 12 shows the amino acid sequence of a peptide isolated from the acidic repeat protein.

SEQ ID NO: 13 shows the amino acid sequence of a peptide isolated from the acidic repeat protein.

SEQ ID NO: 14 shows the amino acid sequence of a peptide isolated from the acidic repeat protein.

SEQ ID NO: 15 shows the amino acid sequence of a peptide isolated from the acidic repeat protein and corresponding to amino acids 168 to 187 of SEQ ID NO: 2.

SEQ ID NO: 16 shows the amino acid sequence of a peptide isolated from the acidic repeat protein.

SEQ ID NO: 17 shows the amino acid sequence of a peptide isolated from the acidic repeat protein.

SEQ ID NO: 18 shows the amino acid sequence of a peptide isolated from the acidic repeat protein.

SEQ ID NO: 19 shows the nucleic acid sequence (GenBank Accession No. AF411124) for the acidic repeat protein gene of *T. pallidum* subspecies *pallidum* Nichols strain. This sequence is similar to SEQ ID NO: 1, but reflects a sequence variation at position 691 of SEQ ID NO: 19.

SEQ ID NO: 20 shows the amino acid sequence of the protein encoded by the acidic repeat protein gene of *T. pallidum* subspecies *pallidum* Nichols strain.

SEQ ID NO: 21 shows the nucleic acid sequence (GenBank Accession No. AF411126) for the acidic repeat protein gene of *T. pallidum* subspecies *pertenue*, CDC-2 strain. This sequence is similar to SEQ ID NO: 3, but reflects that there is a single base (adenine) insertion at position 693 of SEQ ID NO: 3.

SEQ ID NO: 22 shows the amino acid sequence of the protein encoded by the acidic repeat protein gene of *T. pallidum* subspecies *pertenue*, CDC-2 strain.

SEQ ID NO: 23 shows the nucleic acid sequence (GenBank Accession No. AF342806) for the acidic repeat protein gene of *T. pallidum* subspecies *endemicum*, Bosnia strain. This sequence is similar to SEQ ID NO: 5, but reflects that there is a single base (adenine) insertion at position 933 of SEQ ID NO: 5.

SEQ ID NO: 24 shows the amino acid sequence of the protein encoded by the acidic repeat protein gene of *T. pallidum* subspecies *endemicum*, Bosnia strain.

SEQ ID NO: 25 shows the nucleic acid sequence (GenBank Accession No. AF342807) for the acidic repeat protein gene of *T. pallidum* subspecies *pertenue*, CDC-1 strain.

SEQ ID NO: 26 shows the amino acid sequence of the protein encoded by the acidic repeat protein gene of *T. pallidum* subspecies *pertenue*, CDC-1 strain.

DETAILED DESCRIPTION

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure. The entire text of the references mentioned herein is hereby incorporated in their entireties by reference.

The terms "a," "an" and "the" as used herein are understood to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

As used herein, the term "soluble" means partially or completely dissolved in an aqueous solution.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprises" means "includes." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of Peptides and Proteins for Use in Detection of *T. pallidum*

Figure 1:
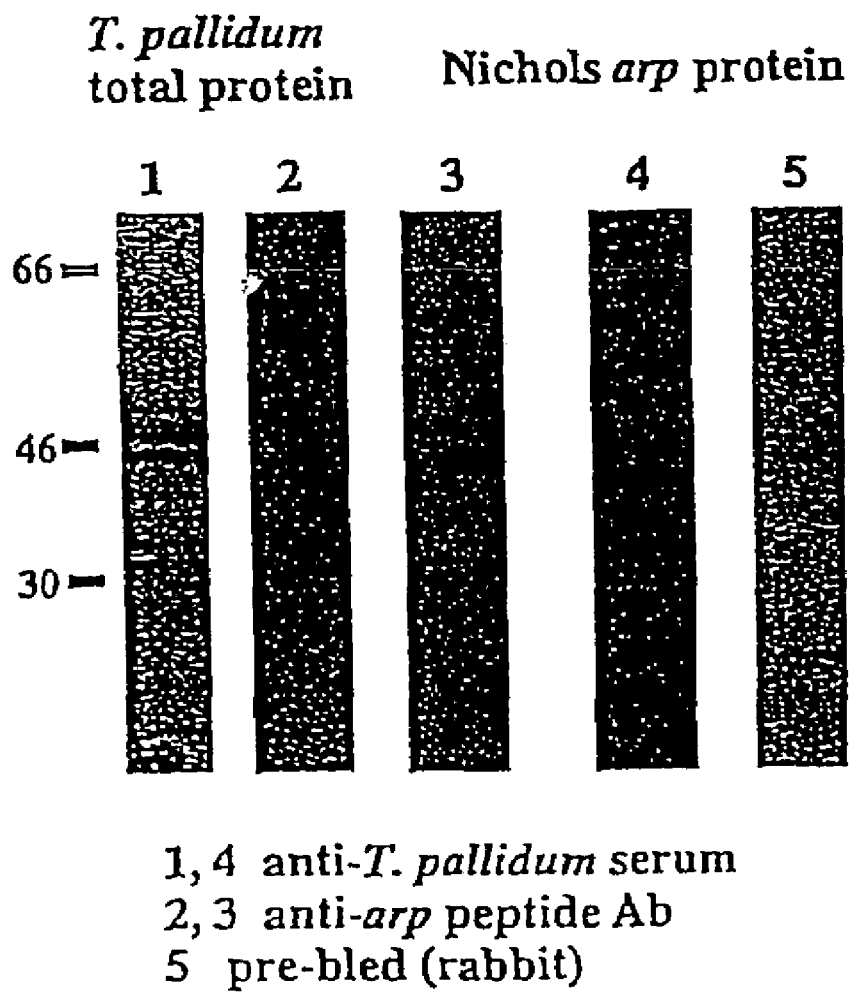
FIG. 1 is a schematic representation of a Western Blot gel showing the ability of syphilitic rabbit sera to recognize the recombinant acidic repeat protein (arp) protein.

Disclosed methods include the use of previously unidentified antigenic proteins that are utilized in detection assays for diagnosing diseases caused by *T. pallidum* infection, primarily syphilis. Although a large number of protein products from *T. pallidum* have been previously utilized in diagnosis of syphilis, specific proteins particularly useful for accurate, early diagnosis of syphilis, or differential diagnosis of syphilis, yaws and bejel, were heretofore unidentified.

Proteins specifically utilized in previous syphilis assays include a 47 kD lipoprotein, a 17 kD lipoprotein and a 15 kD lipoprotein, most of which appeared to be anchored in the cytoplasmic membrane usually by lipid modification of the protein and anchored through the resulting amino terminal lipid moieties. Although all of these proteins are present in large amounts in *T. pallidum*, and although they are highly antigenic, a serious drawback in their use for diagnosis is that they comprise major proteins responded to in the whole treponeme, and thus do not give a positive diagnosis any faster than using whole treponemal cells.

Not wishing to be bound by theory, it is believed that the unusual outer membrane structure of *T. pallidum* causes a significant delay in host response to syphilis infection and therefore early cases of primary syphilis often show negative treponemal serology. The outer membrane, or envelope, of *T. pallidum* appears to be composed mainly of lipids with only a very small number of proteins. Furthermore, it is believed that proteins anchored in the cytoplasmic membranes are shielded from the host immune system, resulting, therefore, in a delayed or diminished immune response. Consequently, detection assays based on membrane-anchored proteins often show a delay in serological reactivity, with some primary syphilis patients producing false negative results.

In contrast to the proteins previously utilized in *T. pallidum* detection assays, the proteins and peptides disclosed herein enable accurate diagnosis of *T. pallidum* infection at early stages. Not wishing to be bound by theory, it is believed that detection of secreted proteins according to the methods disclosed herein overcomes previous problems associated with the structure of the *T. pallidum* outer membrane, and is therefore advantageous over prior assays that rely upon cloned, membrane-shielded antigens. Furthermore, secreted antigenic proteins are more likely to generate a detectable immune response as compared to membrane-shielded antigens, thereby facilitating diagnosis by recognition of corresponding antibodies. In addition, the repeated nature of the proteins render them extremely antigenic and, thus, suitable for early detection of syphilis.

Early detection is crucial for treatment as it can prevent subsequent deterioration to secondary and tertiary forms of syphilis that are marked by more severe and difficult to treat symptoms. Therefore, the methods disclosed herein address the need for early detection of primary syphilis, which until now has been a serious problem area in syphilis serology.

The Nichols strain of *T. pallidum* is the type strain of *T. pallidum* subspecies *pallidum*. As described herein, this strain contains unique repetitive sequences that are each 60 base pairs long, resulting in a protein that contains fourteen repeats, each composed of 20 amino acids within the body of the protein (see FIGS. 6 and 14). The repeat region contains 6 codons for glutamic acid and it is estimated that the protein product has a pI of approximately 4.63, hence the name acidic repeat protein (or arp). There is some minor variation in the 20 amino acid repeats, but the repeats are at least 90% conserved except for the last two repeats in the Nichols strain (rare substitutions are generally conservative). Nucleotide sequences of the acidic repeat protein of this subspecies are disclosed herein as SEQ ID NOs: 1 and 19 (see also FIG. 5), and amino acid sequences are disclosed herein as SEQ ID NOs: 2 and 20 (see also FIGS. 6 and 14).

Figure 2:
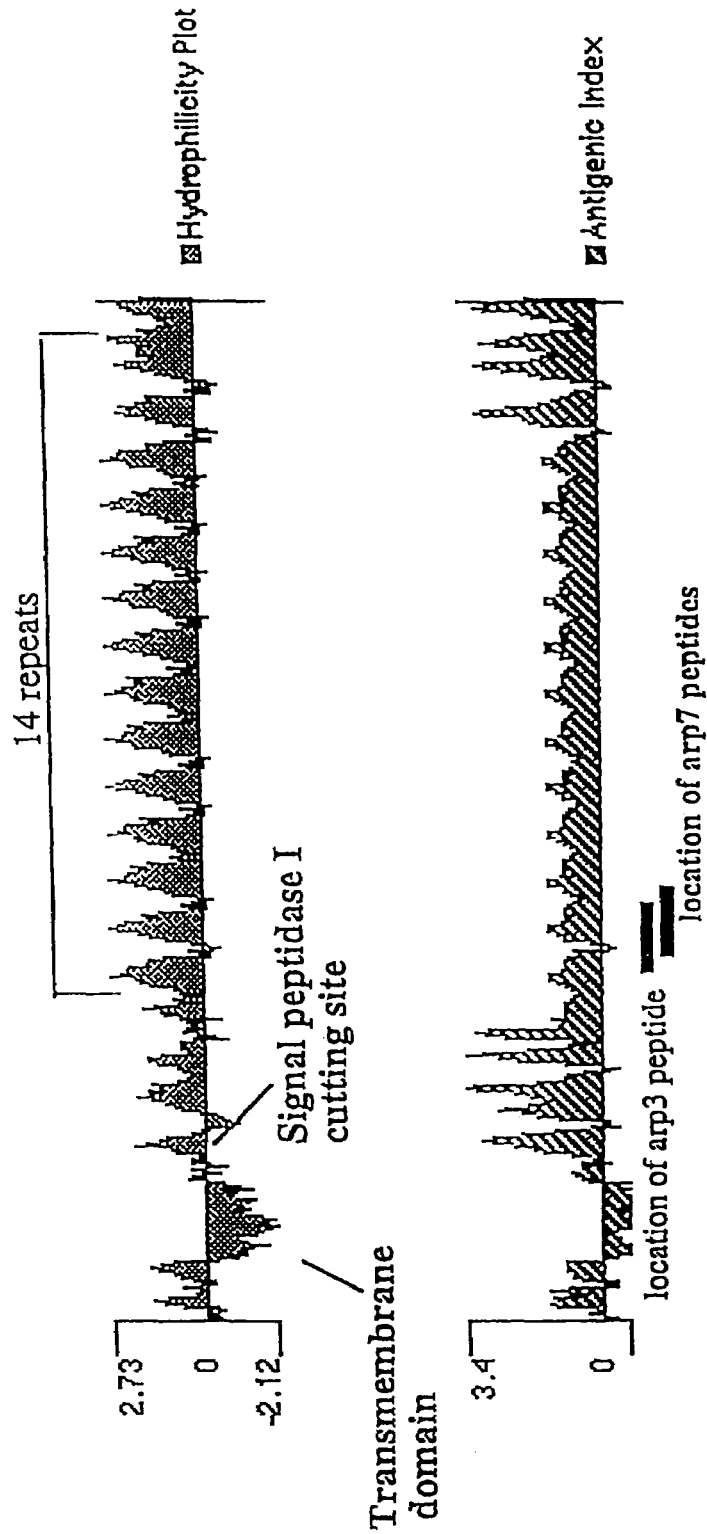
FIG. 2 shows the structure of an acidic repeat protein showing the potential membrane-spanning domain, the potential location of the signal peptidase I cutting site, the hydrophilicity plot of the protein and the potential antigenic index of the protein.

Not wishing to be bound by the following theory, it is believed that the arp gene product, the acidic repeat protein, comprises a protein that exists in a membrane-anchored form or a secreted form. The structural characteristics of the acidic repeat protein are shown in FIG. 2, which is a hydrophobicity profile of the protein including the sequence of one of the repeat elements from the Nichols strain of *T. pallidum*. The protein has a slightly basic amino terminus followed by a hydrophobic stretch of amino acids that may constitute a membrane-spanning domain for the membrane-anchored form. Four consecutive alanines occur shortly after the end of the potential membrane-spanning domain, which is a potential site for signal peptidase I cleavage. In the Nichols strain of *T. pallidum*, the majority of the remainder of the protein is composed of repeat sequences that constitute approximately two-thirds of the total reading frame in this strain.

Active portions of immunogenic regions of the acidic repeat protein can be identified by isolating or synthesizing truncated peptides from the acidic repeat protein and testing the peptides for immunogenic activity using techniques and methods known to those skilled in the art. For example, a protein or peptide for use in accordance with the methods disclosed herein includes the acidic repeat protein encoded by the nucleotide sequence set forth in SEQ ID NOs: 1 and 19, or an immunogenic fragment thereof. Herein disclosed as SEQ ID NO: 7 through SEQ ID NO: 18 are several active portions of an immunogenic domain of acidic repeat protein.

By way of example, active portions of the acidic repeat protein comprise in one embodiment amino acids 128 to 407 of the protein as set forth in SEQ ID NO: 2 in another embodiment amino acids 168 to 187 as set forth in SEQ ID NO: 2, and in yet another embodiment, the peptide having the amino acid sequence set forth in SEQ ID NO: 15.

In another embodiment, a protein or peptide for use in accordance with the methods disclosed herein includes an immunogenic fragment of the acidic repeat protein, having the amino acid sequence set forth in SEQ ID NO: 15.

In an alternative embodiment, a protein or peptide for use in accordance with the methods disclosed herein includes an immunogenic fragment of the acidic repeat protein, arp 3 peptide, having the amino acid sequence set forth in SEQ ID NO: 9.

In another embodiment, a peptide for use in accordance with the methods disclosed herein includes an active fragment of the acidic repeat protein having the amino acid sequence set forth in SEQ ID NO: 13.

In yet another embodiment, peptides for use in accordance with the methods disclosed herein include an active fragment of the acidic repeat protein having the amino acid sequence set forth in any of SEQ ID NOs: 7-18.

One of ordinary skill in the art will recognize that individual substitutions, deletions, or additions that alter, add or delete a single amino acid or a small percentage of amino acids (typically less than 5%, more typically less than 1%) in an encoded sequence are conservatively modified variations in which the alterations result in the substitution of an amino acid with a chemically similar amino acid. Such alterations are within the scope of the disclosure.

In accordance with one embodiment, a sample is combined with antibodies specific for a protein or peptide product of the repeat gene sequence under conditions suitable to formation of an antibody-antigen complex. Detection of the complex using antigen capture methods indicates the presence of *T. pallidum* in a subject. Alternatively, detection of the antigen-antibody complex using antigen as the probe is indicative of the presence of previous or present infection with *T. pallidum*. In certain examples of such methods, the protein product of the repeat gene sequence is the acidic repeat protein or an antigenic peptide fragment thereof.

Peptides or Protein Fragments

The acidic repeat protein can be isolated from *T. pallidum* organisms, or synthesized by chemical or biological methods known to those of skill in the art, such as cell culture, recombinant gene expression, and peptide synthesis as described in the Examples. Recombinant techniques include, for instance, gene amplification from DNA sources using the polymerase chain reaction (PCR), and gene amplification from RNA sources using reverse transcriptase/PCR.

Acidic repeat protein can be produced according to the methods described above and tested for immunogenic or antigenic activity using techniques and methods known to those skilled in the art. For example, full length recombinant acidic repeat protein can be produced using the baculovirus gene expression system or using *E. coli* transformed with the expression vector plasmid containing a complete arp gene. Full length proteins can be cleaved into individual domains or digested using various methods such as, for example, the method described by Enjyoji et al. (*Biochemistry* 34:5725-5735, 1995). In accordance with the method of Enjyoji et al., recombinant acidic repeat protein may be treated with a digestion enzyme, such as human neutrophil elastase, and the digest purified using a heparin column in order to obtain fragments that may then be tested for immunogenicity.

Alternatively, fragments can be prepared by digesting the entire protein, or large fragments thereof exhibiting immunogenic activity, to remove one amino acid at a time. Each progressively shorter fragment is then tested for immunogenic activity. Similarly, fragments of various lengths may be synthesized and tested for immunogenic activity. By increasing or decreasing the length of a fragment, one skilled in the art may determine the exact number, identity, and sequence of amino acids within the protein that are required for immunogenic activity using routine digestion, synthesis, and screening procedures known to those skilled in the art.

The terms "polypeptide," "peptide," and "protein," as used herein, are interchangeable terms referring to a biomolecule composed of two or more amino acids linked by a peptide bond. "Peptides" includes chains of amino acids (typically L-amino acids) wherein alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminus of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids composing a peptide are numbered in order, starting at the amino terminus and increasing in the direction toward the carboxy terminus of the peptide. Thus, when one amino acid is said to "follow" another, that amino acid is positioned closer to the carboxy terminus of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that modifications of a polypeptide that involve the substitution of one or more amino acids for amino acids having similar biochemical properties do not result in change or loss of a biological or biochemical function of the polypeptide. These "conservative substitutions" are likely to have minimal impact on the activity of the resultant protein. In one embodiment, a conservative substitution of an arp region does not change the antigen binding of the peptide. Table 1 shows non-limiting examples of amino acids that may be substituted for an original amino acid in a protein, and which are regarded as conservative substitutions.

TABLE 1

| Original Residue | Conservative Substitutions |
|---|---|
| ala | ser |
| arg | lys |
| asn | gln; his |
| asp | glu |
| cys | ser |

TABLE 1

| Original Residue | Conservative Substitutions |
|---|---|
| gln | asn |
| glu | asp |
| gly | pro |
| his | asn; gln |
| ile | leu; val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. A cDNA sequence variant may, for example, introduce no more than twenty, and for example fewer than ten amino acid substitutions into the encoded polypeptide. Variant amino acid sequences may, for example, be 80, 90 or even 95% or 98% identical to the native amino acid sequence. Programs and algorithms for determining percentage identity can be found at the NCBI website.

The phrases "isolated" or "biologically pure" refer to material that is substantially or essentially free from components that normally accompany it as found in its native state. Thus, the peptides described herein do not contain materials normally associated with their in situ environment. For instance, the isolated, immunogenic peptides described herein may be about 80% pure, at least about 90%, or at least about 95% pure as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is an exemplary method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and so forth. Substantially pure compositions of about 50 to 95% homogeneity are disclosed, and 80 to 95% or greater homogeneity, are disclosed for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the immunogenic peptide and cause the peptide to re-fold into a biologically and biochemically active conformation. Methods of reducing and denaturing proteins and inducing re-folding are well known to those of skill in the art.

Antigenicity of the purified protein may be confirmed, for example, by demonstrating reaction with *T. pallidum* immune serum, or with anti-arp sera produced in a laboratory animal.

The present disclosure provides utility for the protein in diagnosis of syphilis, determination of the state of immunity of the patient, and an assessment of the progress of the disease through recognition of the acidic repeat protein in a subject, by, for example, immunoassays of a biological sample.

One of skill in the art could use the present disclosure to produce desired proteins, for instance the arp protein, in large quantities from cloned genes. As described above, the proteins may then be used in diagnostic assays for syphilis detection through antibody recognition, antigen capture, or for the development of vaccines for treatment of syphilis.

Anti-*T. pallidum* Antigen Antibodies

The terms "antibody" and "antibodies" as used herein include monoclonal antibodies, polyclonal, chimeric, single chain, bispecific, simianized, and humanized antibodies as well as Fab fragments, including the products of a Fab immunoglobulin expression library.

The term "antigen" refers to an entity or fragment thereof that can induce an immune response in a mammal. The term includes immunogens and regions responsible for antigenicity or antigenic determinants.

The antibody provided herein is a monoclonal or polyclonal antibody having binding specificity for a *T. pallidum* antigen including a protein or peptide representative of an immunogenic region. By way of example, a monoclonal antibody could be used to target the arp gene or a member of the arp gene family. As used, the antibody is specific for the arp protein or an antigenic peptide fragment thereof and exhibits minimal or no crossreactivity with other *T. pallidum* proteins or peptides.

A monoclonal antibody of the disclosure may be prepared by immunizing an animal, such as a mouse, rat, or rabbit, with a whole gene product protein, such as the acidic repeat protein or peptides thereof. Spleen cells are harvested from the immunized animals and hybridomas generated by fusing sensitized spleen cells with a myeloma cell line, such as murine SP2/O myeloma cells (ATCC, Manassas, Va.). The cells are induced to fuse by the addition of polyethylene glycol. Hybridomas are chemically selected by plating the cells in a selection medium containing hypoxanthine, aminopterin and thymidine (HAT).

Hybridomas are subsequently screened for the ability to produce monoclonal antibodies against *T. pallidum* immunogenic proteins. Immunogenic proteins used for screening purposes are obtained from analyzed specimens. Alternatively, such proteins may comprise recombinant peptides made according to methods known to those skilled in the art. Hybridomas producing antibodies that bind to the immunogenic protein preparations are cloned, expanded and stored frozen for future production. An example hybridoma of the disclosure produces a monoclonal antibody having the IgG isotype.

Polyclonal antibodies are prepared by immunizing animals, for instance mice or rabbits, with the immunogenic proteins or peptides described above. Blood is subsequently collected from the animals, and antibodies in the sera screened for binding reactivity against the immunogenic proteins, including antigens that react with the monoclonal antibody described above.

The monoclonal antibody, the polyclonal antibody, or both antibodies may be labeled directly with a detectable label for identification *T. pallidum* in a biological sample as described below. Labels for use in immunoassays are generally known to those skilled in the art (e.g., enzymes, radioisotopes, fluorescent, luminescent and chromogenic substances, colored particles, such as colloidal gold, and latex beads). The antibodies may also be bound to a solid phase to facilitate separation of antibody-antigen complexes from non-reacted components in an immunoassay. Exemplary solid phase substances include, but are not limited to, microtiter plates, test tubes, magnetic, plastic or glass beads and slides. Methods for coupling antibodies to solid phases are well known to those skilled in the art.

Alternatively, the antibody may be labeled indirectly by reaction with labeled substances that have an affinity for immunoglobulin, such as proteins A or G or a secondary antibody. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

In one embodiment, the antibody is labeled indirectly by reactivity with a second antibody that has been labeled with a detectable label and that binds to antibodies of the animal from which the monoclonal antibody is derived. For example, if the monoclonal antibody is a mouse antibody, then the labeled, second antibody is an anti-mouse antibody. By way of example, a monoclonal antibody for use in the assay described herein is labeled with an antibody-coated bead, for instance a magnetic bead. A polyclonal antibody for use in the immunoassay described herein can be a detectable molecule, such as a radioactive, fluorescent or an electrochemiluminescent substance.

*T. pallidum* Immunoassay

A highly sensitive *T. pallidum* immunoassay employing one or more of the recombinant or isolated proteins or peptides for detection of *T. pallidum* antibodies described herein is provided. The immunoassay is useful for detecting the presence of *T. pallidum* infection in a variety of samples, for instance biological samples, such as human or animal biological fluids. A biological sample may be obtained from any source in which the *T. pallidum* organism may exist, for instance samples obtained from body cells of a subject, such as those present in wounds, blood, tissues, saliva, semen, vaginal secretions, tears, urine, bone, muscle, cartilage, CSF, skin, or any human tissue or bodily fluid.

In one embodiment, the immunoassay uses an antigenic protein or peptide to detect the presence of *T. pallidum* antibodies. This is achieved by coating the solid phase with the protein or peptides. Subsequently, the biological sample is incubated with the coated surface to allow the binding of antibodies to the protein/peptides. Exemplary condition include, for instance, incubating the biological sample and the coated surface at a temperature above room temperature, such as at a temperature of approximately 20° C. to 45° C. for approximately 10 to 150 minutes. In one embodiment, the biological sample and coated surface are incubated at a temperature of approximately 37° C. for a period of about 60 minutes in the dark. The results of this immunoassay provide a direct indication of *T. pallidum* infection.

It will be understood by those skilled in the art that one or more of the antigens (arp peptides or protein) described above may be employed in any heterogenous or homogeneous (competitive) immunoassay for the detection of *T. pallidum* infection. As described herein, peptides used in the immunoassay of the disclosure are coated to the solid phase, which may comprise any article suitable for such use. Suitable articles are well known to those skilled in the art, and include, but are not limited to, latex particles, filter paper, glass beads, or a commercially available ELISA microtiter plate, such as Immunlon 2HB™ plate available from Dynex Technologies (Chantilly, Va.).

The antigen bound to a solid phase and antibody containing fluid are reacted together for a sufficient amount of time under conditions that promote the binding of antibody to the antigen. It will be understood by those skilled in the art that the immunoassay reagents and samples may be reacted in different combinations and orders.

Physical means can be employed to separate reagents bound to the solid phase from unbound reagents such as filtration of particles, decantation of reaction solutions from coated tubes or wells, magnetic separation, capillary action, and other means known to those skilled in the art. It will be understood that separate washing of the solid phase may be included in the method.

The antigen-antibody complexes formed in the immunoassay disclosed herein are detected using methods known to those skilled in the art. The complexes are exposed to anti-human immunoglobulin antibodies that have been labeled with a detectable marker. Such markers include chemiluminescent, labels, such as horseradish peroxidase; electrochemiluminescent labels, such as FITC; and enzymatic labels, such as alkaline phosphatase, $\beta$-galactosidase, and horseradish peroxidase. The labeled complex is then detected using a detection technique or instrument specific for detection of the label employed. For instance, the complexes can be analyzed with an ELISA reader such as the Ceres 900 HDL (BioTek Instrument, Inc., Winooski, Vt.) for detection of a peroxidase label. Alternatively, a Becton-Dickinson FACS sorter (Franklin Lakes, N.J.) may be used for detection of the FITC label. Soluble antigen or antibodies may also be incubated with magnetic beads coated with non-specific antibodies in an identical assay format to determine the background values of samples analyzed in an assay.

In another embodiment, the immunoassay is designed using the anti-arp monoclonal (or polyclonal) antibodies to detect the presence of arp peptides and/or proteins from *T. pallidum* in biological fluid. A biological sample is incubated to allow binding of the protein or peptide with an antibody, for instance at a temperature above room temperature, for instance approximately 20-45° C. for approximately 10 to 150 minutes, and optionally in the dark. The results of this immunoassay provide a direct indication of the presence of *T. pallidum* infection.

It will be understood by those skilled in the art that one or more of the antibodies described above may be employed in any heterogeneous or homogeneous competitive immunoassay for the detection of *T. pallidum* infection. As mentioned above, for use in the immunoassay provided herein, the antibody is labeled with a detectable label or coupled to a solid phase. By way of example, both a monoclonal antibody and a polyclonal antibody can be used in the assay, for instance with the monoclonal antibody coupled to a solid phase and the polyclonal antibody labeled with a detectable label. The solid phase may comprise any particle suitable for such use known to those skilled in the art, including but not limited to latex particles, filter paper, and glass beads. One non-limiting example of a solid phase is a commercially available ELISA microtiter plate, such as Immunolon 2HB™ plate available from Dynex Technologies (Chantilly, Va.).

In one method of the disclosure, the sample and the antibody bound to a solid phase are reacted together for a sufficient amount of time under conditions that promote the binding of antibody to the immunogenic protein (e.g., the acidic repeat protein) in a sample. It will be understood by those skilled in the art that the immunoassay reagents and sample may be reacted in different combinations and orders. A physical means can be employed to separate reagents bound to the solid phase from unbound reagents such as filtration of particles, decantation of reaction solutions from coated tubes or wells, magnetic separation, capillary action, and other means known to those skilled in the art. It will also be understood that separate washing of the solid phase may be included in the method.

The antibody-antigen complexes formed in the immunoassay of the disclosure can be detected using methods known to those skilled in the art, including but not limited to those employed in sandwich immunoassays and competitive immunoassays. The antibody-antigen complexes are exposed to antibodies similar to those used to capture the antigen, but that have been labeled with a detectable label. Suitable labels include but are not limited to: chemiluminescent labels, such as horseradish peroxidase; electrochemiluminescent labels, such as ruthenium and aequorin; bioluminescent labels, such as luciferase; fluorescent labels such as FITC; and enzymatic labels such as alkaline phosphatase, β-galactosidase, and horseradish peroxidase.

The labeled complex is then detected using a detection technique or instrument specific for detection of the label employed. For instance, the complexes can be analyzed with an ELISA reader such as the Ceres 900 HDL (BioTek Instrument, Inc., Winooski, Vt.) for detection of a peroxidase label. Alternatively, a Becton-Dickinson FACS sorter (Franklin Lakes, N.J.) may be used for detection of the FITC label. Soluble antigen or antigens may also be incubated with magnetic beads coated with non-specific or specific antibodies in an identical assay format to determine the background values of samples analyzed in the assay.

Assay Characteristics

Presently available assays for *T. pallidum* are generally considered inaccurate and inefficient because they require significant processing time and rely upon the detection of antigenic markers that are typically membrane-bound proteins.

The immunoassay provided herein allows for the detection of *T. pallidum* in a sample, thereby permitting a realistic indication of the consequences of infection with regard to manifestation of disease. The methods provided herein detect *T. pallidum* by recognition of secreted antigenic proteins or peptides or antibodies to those proteins or peptides. The advantage of this type of recognition is that the assay is neither dependent upon recognizing the parasite in particulate form or upon detecting the presence of membrane-bound proteins that are usually shielded from the host immune system. Detection based on the presence of secreted protein antigens both increases the sensitivity of the method, and reduces time periods for accurate diagnosis, thereby enabling detection of primary syphilis.

The detection assay described herein is effective because it is based upon the detection of immunogenic or antigenic proteins representative of specific gene sequences or antibodies to those proteins. Unlike previous methods, the detection assays of the present disclosure are not directed to membrane-bound antigenic proteins typically associated with *T. pallidum*. Instead, secreted proteins are detected and thus, the results are not hampered by proteins that are anchored or shielded by the cytoplasmic membrane. Additionally, secreted proteins may be detected earlier because these proteins are more likely to elicit an early immune response as compared to membrane-anchored proteins.

The assay is also valuable for epidemiological reasons as it may be used to identify levels of infection in a subject. For example, high levels of acidic repeat protein may correlate to progressive stages of disease. Knowledge of infection at early stages is especially important because diagnosis of disease at an early stage can lead to effective treatment early on, preventing deterioration into the more serious conditions seen in later stages of the disease.

Differential Diagnosis of *T. pallidum* Infection

In addition to providing the nucleotide and amino acid sequences for *T. pallidum* subspecies *pallidum* (SEQ ID NOs: 1, 2, 19, and 20 and FIGS. 5, 6, and 15), the present disclosure also provides previously unidentified nucleotide and amino acid sequences corresponding to *T. pallidum* subspecies *pertenue*, CDC-2 strain (SEQ ID NOs: 3, 4, 21, and 22, and FIGS. 7, 8 and 15), *T. pallidum* subspecies *endemicum* (SEQ ID NOs: 5, 6, 23, 24, and FIGS. 9, 10 and 16), and *T. pallidum* subspecies *pertenue*, CDC-1 strain (SEQ ID NO: 25 and 26 and FIG. 17). Accordingly, one skilled in the art may employ the methods taught by the present invention for the differential diagnosis of *T. pallidum* infection and thereby identify the causative agent of disease as *T. pallidum* subspecies *pallidum*, *T. pallidum* subspecies *pertenue* (CDC-2 strain), *T. pallidum* subspecies *pertenue* (CDC-1 strain), or *T. pallidum* subspecies *endemicum*. These methods allow for the early detection and identification of infection as it facilitates the control of further dissemination of disease. In addition, specific identification of each of the *Treponema* subspecies enables the development of specific antibodies that may be utilized in therapeutic treatments. An additional advantage of specifically identifying particular subspecies is that the manifestation of particular disease, either syphilis, yaws or bejel, may be anticipated allowing for appropriate measures to be taken to either prevent, or at least diminish, the various symptoms.

Though not wishing to be bound by theory, it is believed that the antibody titers against the arp protein will decline when the organisms have been eliminated. This suggests that assays utilizing arp peptides/proteins for immunodetection of anti-treponemal antibodies are additionally useful in differentiating between current infections and past infections.

Kits for Detection of *T. pallidum*

The arp proteins and peptide fragments described herein are ideally suited for the preparation of a kit. The kit can include a carrier means, such as a box, a bag, or plastic carton. In one embodiment the carrier contains one or more containers, for instance vials, tubes, and the like that include a sample of protein or peptide fragment. In another embodiment, the carrier includes a container with an agent that affects protein or peptide fragment binding, a buffer, or a vehicle for the introduction of the protein or peptide fragment. Instructions can be provided to detail the use of the components of the kit, such as written instructions, video presentations, or instructions in a format that can be opened on a computer (e.g., a diskette or CD-ROM disk). These instructions indicate, for example, how to use the protein or peptide fragment to detect and/or treat *T. pallidum* or how to use the protein or peptide fragment to screen test agents of interest (such as treatment agents). In a further embodiment, one or more control peptides are provided for use in the protein or peptide fragment detection reactions.

The amount of each protein or peptide fragment supplied in the kit can be any appropriate amount, depending for instance on the market to which the product is directed. For instance, if the kit is adapted for research or clinical use, the amount of each protein or peptide fragment provided would likely be an amount sufficient to screen several biological samples. The proteins or peptide fragments can be provided suspended in an aqueous solution or as a freeze-dried or lyophilized powder, for instance. In certain embodiments, the proteins or peptide fragments will be provided in the form of a pharmaceutical composition. In other embodiments, nucleic acids encoding the protein and peptides of the disclosure are provided.

Those of ordinary skill in the art know the amount of protein or peptide fragment that is appropriate for use in a single detection reaction. General guidelines may for instance be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

Kits may additionally include one or more buffers for use during detection procedures. For instance, such buffers may include a low stringency, a high stringency wash, and/or a stripping solution. These buffers may be provided in bulk, where each container of buffer is large enough to hold sufficient buffer for several probing or washing or stripping procedures. Alternatively, the buffers can be provided in pre-measured aliquots, which would be tailored to the size and style of antibody or antigen binding fragment included in the kit.

The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, suggest themselves to those of ordinary skill in the art, without departing from the spirit of the present invention.

EXAMPLE 1

Characteristics of the Acidic Repeat Protein

Genes coding for the acidic repeat proteins from *T. pallidum* (Nichols strain, CDC-1 strain, CDC-2 strain and Bosnia strain) were cloned. The nucleotide sequences are set forth in SEQ ID NOs: 1 (GenBank Accession No. AF015824), 3, 5, 19 (GenBank Accession No. AF411124), 21 (GenBank Accession No. AF411126), 23 (GenBank Accession No. AF342806), and 25 (GenBank Accession No. AF342807). The arp protein of the Nichols strain was predicted to be 59.4 kD. The protein is characterized by a transmembrane domain, a hydrophobic domain (Q26 to V60) at the N-terminus that could span the cytoplasmic membrane, a sequence of four alanines (A45 to A48), which could serve as a potential signal peptidase I processing site, and 14 almost identical repeats (see FIG. 2) of a 20 amino acid sequence. The putative protein is composed of 18.1% glutamic acids (86 of 432 amino acids).

The top portion of FIG. 2 represents the hydrophilicity plot of the protein according to its primary sequence. Most of the protein is hydrophilic, and therefore, though not wishing to be bound by theory, it is believed that this property corresponds to the protein's antigenic index (lower part of the FIG. 2). At the N terminal end, a stretch of hydrophobic amino acids (amino acid 27 to amino acid 43) constitutes the dip in the hydrophilicity plot. This region is the potential membrane-spanning domain. Immediately after the membrane-spanning domain, the sequence contains a potential signal peptidase I cutting site. A significant feature of the arp protein is the 14 almost identical repeats, each about 20 amino acids in length. These repeats are extremely high in glutamic acid accounting for the low predicted pI, 4.63. The repeats were classified into three types according to their similarities. Type II repeats constitute 50% of the total repeats (7 out of 14) and were the predominant type. It is predicted that most of the *T. pallidum* species will have type II repeats. Additional clinical isolates of the arp gene have been sequenced and it has been confirmed that the three types of repeats are universal (see Example 7). Peptides made from this repeat region are especially useful in serodiagnosis.

EXAMPLE 2

Potential Usages of arp Protein in Diagnosis of Syphilis

The following studies were directed to further characterize the arp protein with emphasis on the repeat region of immunogenic peptides. The newly identified immunogenic peptides served as targets for constructing immuno diagnostic kits having improved and superior sensitivity.

Initially, after discovering the arp protein's hydrophilicity plot and its antigenic index as predicted from its protein sequence, peptide fragments from the repeat region of the protein were prepared and used to immunize rabbits. Sera from peptide-immunized rabbits recognized the expressed recombinant protein from an arp gene-containing plasmid. In addition, sera from treponemal infected rabbits also recognized this recombinant protein. (Western blot analyses shown in FIG. 1: Lane 1=total *T. pallidum* protein identified by anti-*T. pallidum* serum; Lane 2=anti-peptide [1,2,3] sera failed to identify arp in total *T. pallidum* protein extracts; Lane 3=recombinant arp protein identified by anti-arp peptide serum; Lane 4=arp protein identified by anti-*T. pallidum* serum; Lane 5=pre-bled (bleeding right before injection of the antigen) control).

EXAMPLE 3

Immune Response Toward Peptides of *T. pallidum* Repeat Protein

Peptides designed from different regions of the arp protein were used (see Table 2). Syphilitic human sera were used in an ELISA assay to determine the reactivity toward these peptide fragments. The syphilitic sera were either rapid plasma reagent (RPR) positive or negative (RPR+ or RPR−) according to commercial RPR test kits. It was discovered that most of the RPR+ sera reacted with arp peptides 3, 7 and 9 vigorously, whereas none of the RPR− sera reacted with any of the peptides. Reactivity was detected at 1:100 dilution despite that most commercial ELISA kits require a dilution of 1:20 to detect reaction.

Figure 3:
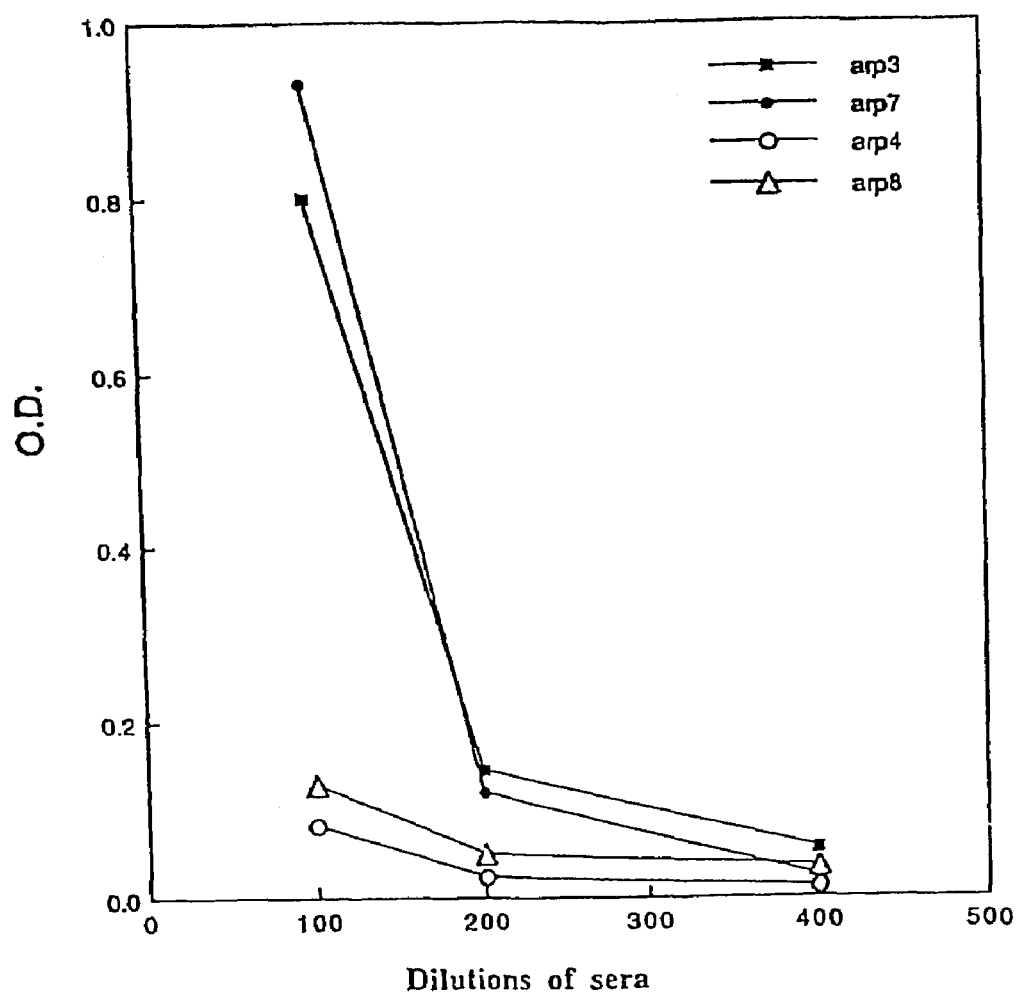
FIG. 3 provides a graph showing the reaction of various peptides isolated from different regions of the acidic repeat protein (solid square represents SEQ ID NO: 9, open circle represents SEQ ID NO: 10, solid circle represents SEQ ID NO: 13, and open triangle represents SEQ ID NO: 14) with syphilitic human sera.
Figure 4:
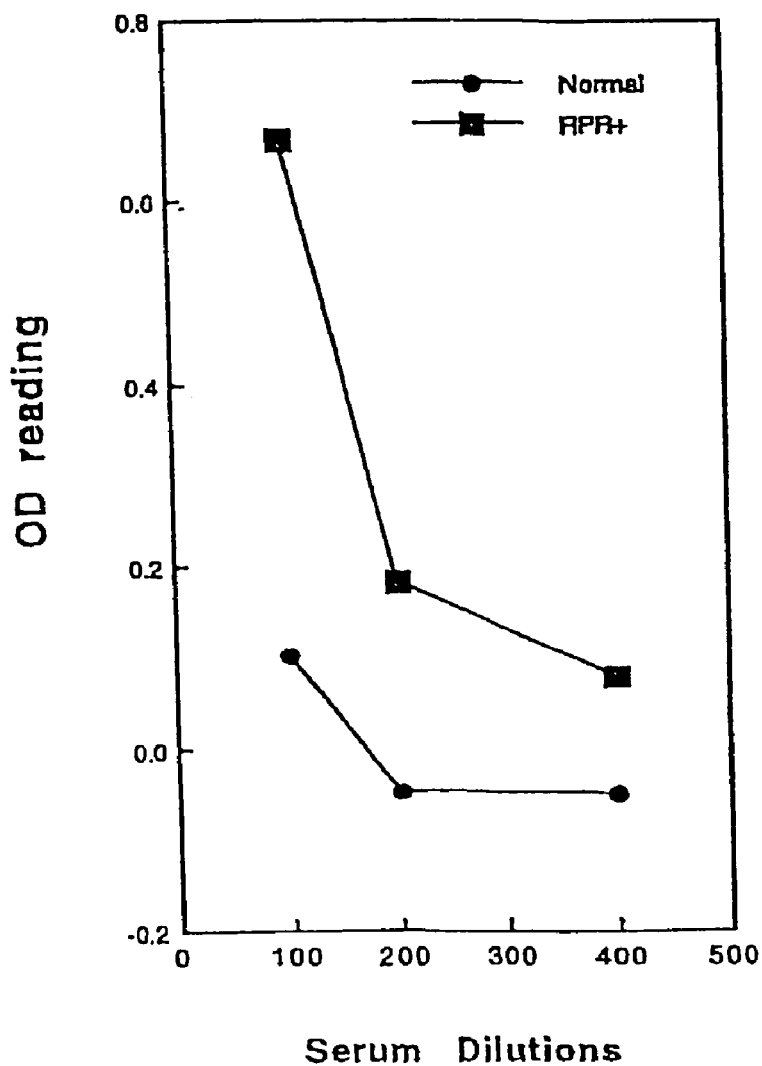
FIG. 4 is a graph showing the results of ELISA to detect the presence of anti-arp antibodies in humans.
Figure 12:
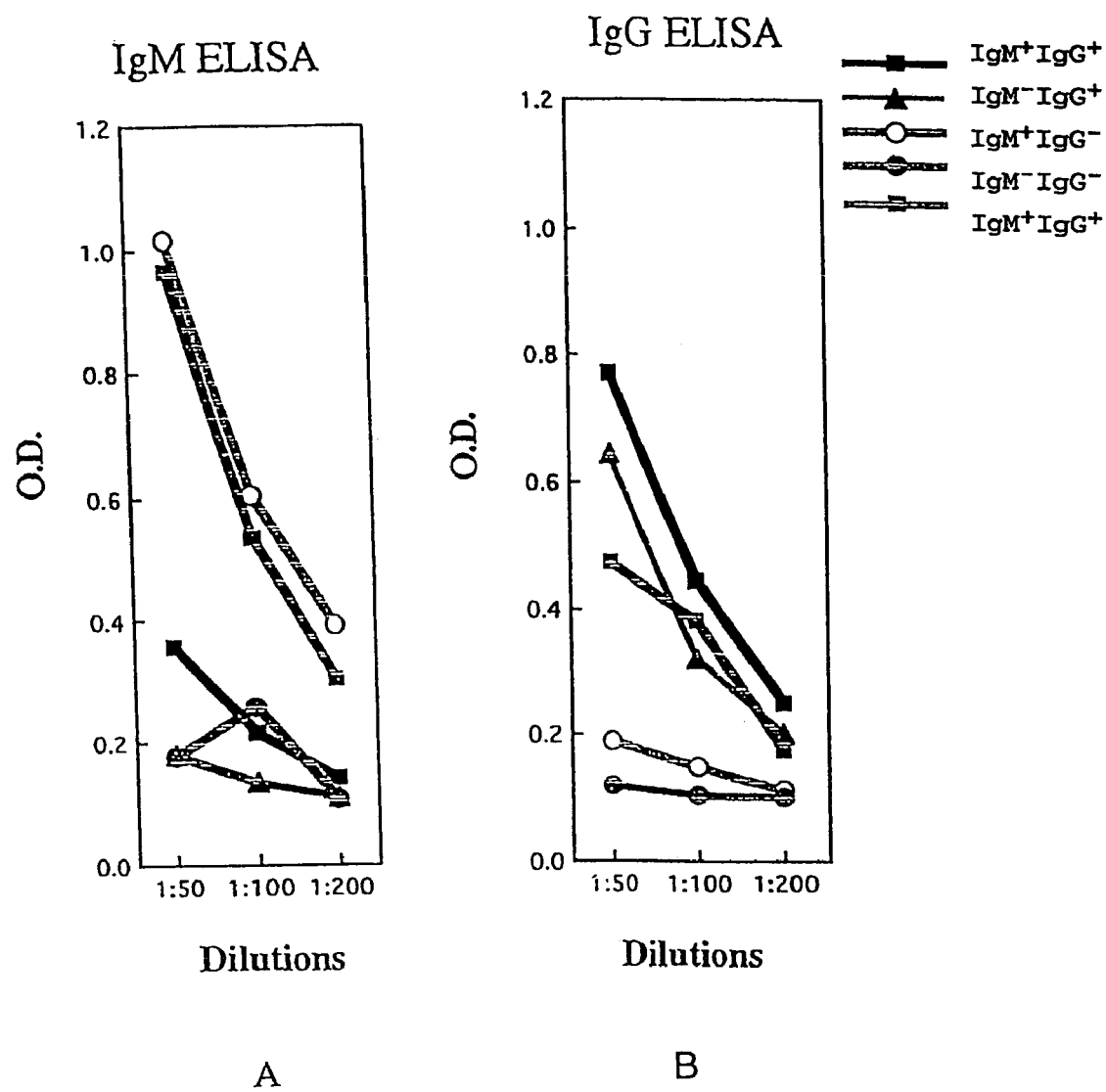
FIG. 12 is two graphs indicating that current syphilis infection (primary syphilis) can be separated into three stages based on serological responses toward arp peptides.
Figure 13:
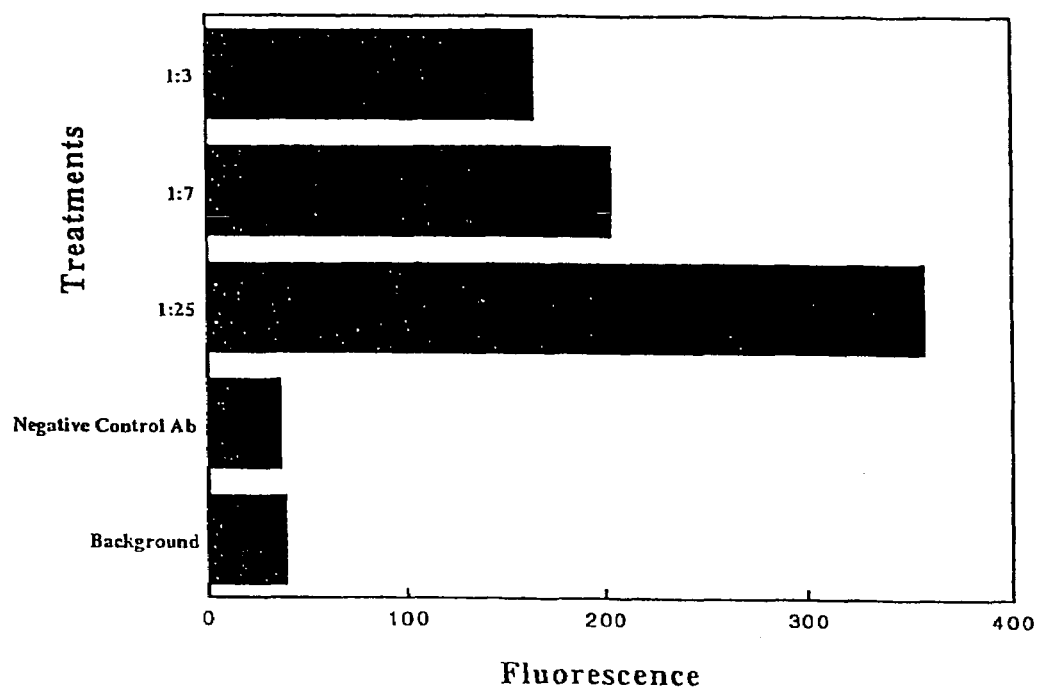
FIG. 13 is a representative graph showing the results of flow cytometric analyses of human syphilitic sera using arp peptides.

Other peptides (peptide 1-12, excluding 3, 7 and 9) were derived either from the N or C terminal ends of arp protein or from type I or III repeats. Immunogenic reactivity was found to be specific in some peptides to the amino acid sequence DVPK. The results of this study are provided in FIG. 3.

TABLE 2

| Peptide # | Amino Acid Sequence | SEQ ID NO: |
|---|---|---|
| arp 1 | LVSPLREVEDAPKVVEPAS | SEQ ID NO: 7 |
| arp 2 | SREVEDAPKVVEPASEREGG | SEQ ID NO: 8 |
| arp 3 | PKVVEPASEREGGEREVEDA | SEQ ID NO: 9 |
| arp 4 | PKNTAVEISNLEKNAKAQAVV | SEQ ID NO: 10 |
| arp 5 | GHAGIPGLLVSLAPAAAAQLGIGVY | SEQ ID NO: 11 |
| arp 6 | VPARPAQRDPLSSPPAGHTVPEYRD | SEQ ID NO: 12 |
| arp 7 | VVEPASEREGGERIEVEDVPKV | SEQ ID NO: 13 |
| arp 8 | VVEPASGHEGGEREVASQHTKQPSHS | SEQ ID NO: 14 |
| arp 9 | EVEDVPKVVEPASEREGGER | SEQ ID NO: 15 |
| arp 10 | EVENVPKVVEPASEREGGER | SEQ ID NO: 16 |
| arp 11 | EVEDAPKVVEPASEREGGER | SEQ ID NO: 17 |
| arp 12 | EVEDVPGVVEPASGHEGGER | SEQ ID NO: 18 |

EXAMPLE 4

Sequence comparisons between the arp Proteins of *T. pallidum* Subspecies

The arp genes of two type strains, CDC-2 and Bosnia, from each of the *T. pallidum* subspecies, *T. pallidum* ssp. *pertenue* and *T. pallidum* ssp. *endemicum*, were cloned and tested. The gene sequences showed significant homology with the Nichols strain of *T. pallidum* ssp. *pallidum*. The 5' end and 3' end of the genes of the three subspecies are completely identical, while the repeat regions showed some variations. The interesting observation was that the translated arp protein of the two subspecies showed a single type of repeat, type II, which is the predominant type in the Nichols strain. This finding confirms that those peptides synthesized in regions with the predominant type of repeat (type II) are immunogenic (as shown in FIG. 4). The other repeats (types I and III) are also immunogenic.

Modifications and variations of the present method will be obvious to those skilled in the art from the foregoing detailed description. Such modifications and variations are intended to come within the scope of the appended claims.

EXAMPLE 5

ELISA Assay Using Arp Peptide Classified Syphilitic Infection in Two Different Stages Peptide arp #9 (SEQ ID NO: 15) was used in this experiment (FIG. 12). Sera from patients with current syphilitic infection were tested in an ELISA assay. All patients in this study had positive PCR reaction in their ulcer specimens. It was found that patients can be classified into early infection (IgM positive), intermittent infection (both IgM and IgG positive) and late infection (IgG positive only).

EXAMPLE 6

Rapid Flowmetric analyses of Syphilitic Infection

Flow cytometry is routinely used in immunologic laboratories. The LUMINEX™ system allows for diagnosis of multiple diseases and disease markers to be easily multiplexed. Current tests that have been developed or are under development include human cytokines (IL-2, 3, 4, 6, etc.) and viral and bacterial infections (HIV, hepatitis, etc.). Arp #9 peptides were coupled to biotin molecule. This biotinylated peptide is further bound to strepavidin beads, such as those that are available from LUMINEX™. Two sera were tested in this system. It was clear that the RPR+ sera reacted strongly in the assay, whereas RPR-normal sera have very low background level of fluorescent response (FIG. 13). This result demonstrated the possibility of multiplexing our arp peptide beads with other clinical tests using the LUMINEX™ multiplex bioassay detection system.

EXAMPLE 7

Detection of Variability in the arp Genes

To further demonstrate inter-strain variability of arp genes, using methods essentially as described herein, laboratory strains of all three subspecies of *T. pallidum* and some clinical strains of *T. pallidum* subspecies *pallidum* were examined. The following was observed (summarized in Table 3):

Multiple clones were discovered in each clinical isolate, clearly demonstrating intra-strain heterogeneity. Three types of repeats, types I, II, and III, were consistently found in the various isolates.

All clinical isolates of *T. pallidum* ended with type III repeats, with one exception, ending in I/III hybrid repeats. Type II repeats were observed only in *T. pertenue* and *T. endemicum*. This further supports the discovery that type II vs. type III repeats can be used for the differentiation of *Treponema* species.

In clinical isolates of *T. pallidum*, a hybrid repeat II/III was observed toward the end of the repeat region. Though this type of repeat might be classified as a new repeat type, it conforms to the previously observed repeat types. In addition, one unique clone was isolated derived from the Nichols strain, in which the repeat region ended in I/III hybrid repeat type.

TABLE 3

Sequencing Results Summary

| | | Original Repeat No. | Number of Clones | Observed Repeat Numbers (Intra-strain variations) |
|---|---|---|---|---|
| Laboratory Strains | | | | |
| *T. pallidum*, Nichols | | 14 | 4 | 1, 4, 9, 14 |
| *T. pertenue*, CDC1 | | 6 | 1 | 6 |
| *T. pertenue*, CDC2 | | 4 | 5 | 4 |
| *T. endemicum*, Bosnia | | 8 | 5 | 6, 8 |
| Clinical Isolates | | | | |
| *T. pallidum* | I | 14 | 4 | 4,14 |
| | II | 14 | 4 | 14 |
| | III | 14 | 1 | 14 |
| | IV | 14 | 1 | 14 |
| | V | 14 | 1 | 3 |
| | VI | 14 | 1 | 4 |

In addition, several mutational hot spots were observed; it is believed that these can serve as immunological epitopes. Overall, the mutations at these hotspots either involved a change to Glycine or were completely conserved (S->S). Most mutations involved the second base pair with the exception of completely conserved mutations (either G->G or S->S) involving the third base pair. The following is a summary of these mutational hotspots:

Semi-Conserved Mutations:

Ni 3-2, repeat No 4, GAC (E)-->GGC (G)
Bal 9-2, repeat No 10, GAC (D)-->GGC (G)
AZ 3-2, repeat No 12, GAG (E)-->GGG (G)

Completed Conserved Mutations:

AZ 6-1, repeat No. 12, GGA (G)-->GGG (G)
AZ 6-1, repeat No. 14, TCT (S)-->TCC(S)
AZ 2-4, repeat No. 14, TCT (S)-->TCC(S)

This disclosure provides methods for detection of *T. pallidum*. It will be apparent that the precise details of the methods and compositions described may be varied or modified without departing from the spirit of the described invention. We claim all such modifications and variations that fall within the scope and spirit of the claims below.

The invention claimed is:

1. An isolated polypeptide consisting of the amino acid sequence set forth in SEQ ID NO: 20.

* * * * *

UNITED STATES PATENT AND TRADEMARK OFFICE
CERTIFICATE OF CORRECTION

PATENT NO. : 7,335,736 B2 Page 1 of 1
APPLICATION NO. : 11/221263
DATED : February 26, 2008
INVENTOR(S) : Liu et al.

It is certified that error appears in the above-identified patent and that said Letters Patent is hereby corrected as shown below:

On the title page, item [54]:
"*PALIDUM*" should read --*PALLIDUM*--

Column 1, line 2 "*PALIDUM*" should read --*PALLIDUM*--

Signed and Sealed this

Twenty-third Day of September, 2008

JON W. DUDAS
*Director of the United States Patent and Trademark Office*

SEQUENCE LISTING

```
<160> NUMBER OF SEQ ID NOS: 26

<210> SEQ ID NO 1
<211> LENGTH: 2945
<212> TYPE: DNA
<213> ORGANISM: Treponema pallidum
<220> FEATURE:
<221> NAME/KEY: CDS
<222> LOCATION: (919)..(2217)
<223> OTHER INFORMATION:
<220> FEATURE:
<221> NAME/KEY: misc_feature
<223> OTHER INFORMATION: Subspecies:  pallidum (Nichols strain)

<400> SEQUENCE: 1
gtcgatgcac agctgacgct ctcaggtctt gcacatattg cgcggctggt gccgacatct      60
ctcctgccac ctgctacagt gtcaggttca tcggggaatt gaggaaactg ttatccgcgc     120
tccccatctt ccgatactgg atcggtgtcg gggggagtag gagtgggggaa gcgtctgtgc    180 tgtatcgcgc tggtgatgcg cgcgttctgg tacctcagtg cgaagggagt cagtatcgct     240
tacgtgcccg ttcatcgcag tgggggctct caagattcga gcatgagcac agcagtgggc     300
gatacgctcc ttaacgcctt cttcgacgag ggaatggtgg ttacggcagt accgccgggt     360
gtacacgacg gccagactat agcagaaatt gctgcatgtt ttgaagtaat gcccgattac     420
gcgttgttgg tgcagtttca ttccgctcgt ctccctggtg gggaaagccc tacctcccgt     480
gcccgcggcg cttggtcttc agagaggttc cgtgctgtgt ggacattagt ggatttgcat     540
acgcagcgcg cgtgtgtcta tgcgtgtgtc gccccataca gggagagtat tcccgtttct     600
gagtgtgttg acgtcgttac ccgttgtatt gcggagcagg caatttcgta catacggggtg    660 ggcacgagca ccgatacagc cggagttcag ttatagaaaa tagggaatac gtaaggtgtc     720
tgcagcgtcg cttcagctgg gaggagtctt atgattaaac gccacatgtt cgcaaaaagg     780
ggtgtcaaag gaagatctta cctggttagg gtgaacactg cgttcttagt gctttgtgtt     840
gcttctgtca cgccgctttg ggctgtgtgg gaagggaatg cagaaattgg cccccaggga     900
agttttctgc aggacggc atg ttt gtg cgc agt gac atg ttc ccc aaa aac       951
                    Met Phe Val Arg Ser Asp Met Phe Pro Lys Asn
                    1               5                  10 act gct gtt gaa att agc aac tta gaa aag aat gcc aag gct cag gca       999
Thr Ala Val Glu Ile Ser Asn Leu Glu Lys Asn Ala Lys Ala Gln Ala
             15                  20                  25 gtg gtt att ggg cac gca ggg atc ccc ggt ctt cta gtt agc ctt gca      1047
Val Val Ile Gly His Ala Gly Ile Pro Gly Leu Leu Val Ser Leu Ala
         30                  35                  40 ccc gct gct gca gca cag ctt ggg att ggc gta tac caa gct gtg cgt      1095
Pro Ala Ala Ala Ala Gln Leu Gly Ile Gly Val Tyr Gln Ala Val Arg
     45                  50                  55
```

```
gta cgc gta cgt acc ttg ggt acc gtg cgc ggt ggg tct caa aca agt      1143
Val Arg Val Arg Thr Leu Gly Thr Val Arg Gly Gly Ser Gln Thr Ser
60              65                  70                  75 cag gac gga ctg tcc ctt gca tct ttg ccg tcc cgt gtg cct gcg cgc      1191
Gln Asp Gly Leu Ser Leu Ala Ser Leu Pro Ser Arg Val Pro Ala Arg
                80                  85                  90 ccc gcg cag cgt gat cct ctg tca tcc ccg gca ggt cac act gta          1239
Pro Ala Gln Arg Asp Pro Leu Ser Ser Pro Pro Ala Gly His Thr Val
            95                  100                 105 ccg gaa tat cgc gat acg gtt att ttc gat gac ccg cgt ttg gtt tcc      1287
Pro Glu Tyr Arg Asp Thr Val Ile Phe Asp Asp Pro Arg Leu Val Ser
        110                 115                 120 cct ttg tct cgt gag gtg gag gac gcg ccg aag gta gtg gag ccg gcc      1335
Pro Leu Ser Arg Glu Val Glu Asp Ala Pro Lys Val Val Glu Pro Ala
    125                 130                 135 tct gag cgt gag gga ggg gag cgt gag gtg gag gac gcg ccg aag gta      1383
Ser Glu Arg Glu Gly Gly Glu Arg Glu Val Glu Asp Ala Pro Lys Val
140                 145                 150                 155 gtg gag ccg gcc tct gag cgt gag gga ggg gag cgt gag gtg gag gac      1431
Val Glu Pro Ala Ser Glu Arg Glu Gly Gly Glu Arg Glu Val Glu Asp
                160                 165                 170 gtg ccg aag gta gtg gag ccg gcc tct gag cgt gag gga ggg gag cgt      1479
Val Pro Lys Val Val Glu Pro Ala Ser Glu Arg Glu Gly Gly Glu Arg
            175                 180                 185 gag gtg gag gac gcg ccg aag gta gtg gag ccg gcc tct gag cgt gag      1527
Glu Val Glu Asp Ala Pro Lys Val Val Glu Pro Ala Ser Glu Arg Glu
        190                 195                 200 gga ggg gag cgt gag gtg gag gac gtg ccg aag gta gtg gag ccg gcc      1575
Gly Gly Glu Arg Glu Val Glu Asp Val Pro Lys Val Val Glu Pro Ala
    205                 210                 215 tct gag cgt gag gga ggg gag cgt gag gtg gag aac gtg ccg aag gta      1623
Ser Glu Arg Glu Gly Gly Glu Arg Glu Val Glu Asn Val Pro Lys Val
220                 225                 230                 235 gtg gag ccg gcc tct gag cgt gag gga ggg gag cgt gag gtg gag gac      1671
Val Glu Pro Ala Ser Glu Arg Glu Gly Gly Glu Arg Glu Val Glu Asp
                240                 245                 250 gcg ccg aag gta gtg gag ccg gcc tct gag cgt gag gga ggg gag cgt      1719
Ala Pro Lys Val Val Glu Pro Ala Ser Glu Arg Glu Gly Gly Glu Arg
            255                 260                 265 gag gtg gag gac gcg ccg aag gta gtg gag ccg gcc tct gag cgt gag      1767
Glu Val Glu Asp Ala Pro Lys Val Val Glu Pro Ala Ser Glu Arg Glu
        270                 275                 280 gga ggg gag cgt gag gtg gag gac gtg ccg aag gta gtg gag ccg gcc      1815
Gly Gly Glu Arg Glu Val Glu Asp Val Pro Lys Val Val Glu Pro Ala
    285                 290                 295 tct gag cgt gag gga ggg gag cgt gag gtg gag gac gtg ccg aag gta      1863
Ser Glu Arg Glu Gly Gly Glu Arg Glu Val Glu Asp Val Pro Lys Val
300                 305                 310                 315 gtg gag ccg gcc tct gag cgt gag gga ggg gag cgt gag gtg gag gac      1911
Val Glu Pro Ala Ser Glu Arg Glu Gly Gly Glu Arg Glu Val Glu Asp
                320                 325                 330 gtg ccg aag gta gtg gag ccg gcc tct gag cgt gag gga ggg gag cgt      1959
Val Pro Lys Val Val Glu Pro Ala Ser Glu Arg Glu Gly Gly Glu Arg
            335                 340                 345 gag gtg gag gac gtg ccg aag gta gtg gag ccg gcc tct gag cgt gag      2007
Glu Val Glu Asp Val Pro Lys Val Val Glu Pro Ala Ser Glu Arg Glu
        350                 355                 360 gga ggg gag cgt gag gtg gag gac gtg ccg ggg gta gtg gag ccg gcc      2055
Gly Gly Glu Arg Glu Val Glu Asp Val Pro Gly Val Val Glu Pro Ala
    365                 370                 375
```

-continued

```
tct ggg cat gaa gga ggg gag cgt gag gtg gag gac gtg ccg ggg gta      2103
Ser Gly His Glu Gly Gly Glu Arg Glu Val Glu Asp Val Pro Gly Val
380             385                 390                 395 gtg gag ccg gcc tct ggg cat gaa gga ggg gag cgt gag gtc gct tct      2151
Val Glu Pro Ala Ser Gly His Glu Gly Gly Glu Arg Glu Val Ala Ser
            400                 405                 410 cag cat acg aag cag cca tcc cac tcg gtt tcc aac tca gct ccc aat      2199
Gln His Thr Lys Gln Pro Ser His Ser Val Ser Asn Ser Ala Pro Asn
        415                 420                 425 cag ttt cgg aaa ccc tga ggggaactc ccctttacgc tccctgacct              2247
Gln Phe Arg Lys Pro
        430 atccgagtca gaaattgtgg ttccggagga acagaaagga cgtgcgcatc cccaggtgat    2307 acccgagggt gcgccacgtg gactgcaacc tggtgaatac tacgtacaga ttgcagtctt    2367 tcatgacgct atccaggtgc agagcattgt ccaccgttac ggggtagaat accccatcgc    2427 agtggagcag gacatccatg aaggtaaggt gcgtttcacc gtatgcgtcg gtcctgtcca    2487 aaaagacgaa cgcggcgcgg tactagagaa cttccaaagg tttggattca aggacgcctt    2547 tctgaaaaag gcgcgatgat caggtcggcc ctcctcttcc cctcgtgacc gtggtgactc    2607 gccccgaagg gggcgcacag agcccgaagg aacggaaggg aagggcagca cttaactatt    2667 tctttgtttt tttgagcacg taaaacggcg ccatctcctt tgaaggcttt cctgcgccgg    2727 gagcgcccat gtagcgaacg gagttactgt ctatcagctc gtacagctct ttctcgtgcg    2787 gtgccttcga ttgctccgag gacacaagcg agagttcgaa aattccgtct tcacgtacca    2847 tccacgtacc gcgatacgta agaggagaag gtgccgactt cttctcaagg gcaagctcta    2907 cctttttgcgc agtgccatcc gcgttgaacg tcacagtc                           2945
```

<210> SEQ ID NO 2
<211> LENGTH: 432
<212> TYPE: PRT
<213> ORGANISM: Treponema pallidum
<220> FEATURE:
<221> NAME/KEY: misc_feature
<223> OTHER INFORMATION: Subspecies: pallidum (Nichols strain)

<400> SEQUENCE: 2

```
Met Phe Val Arg Ser Asp Met Phe Pro Lys Asn Thr Ala Val Glu Ile
1               5                   10                  15

Ser Asn Leu Glu Lys Asn Ala Lys Ala Gln Ala Val Val Ile Gly His
            20                  25                  30

Ala Gly Ile Pro Gly Leu Leu Val Ser Leu Ala Pro Ala Ala Ala
        35                  40                  45

Gln Leu Gly Ile Gly Val Tyr Gln Ala Val Arg Val Arg Val Arg Thr
    50                  55                  60

Leu Gly Thr Val Arg Gly Gly Ser Gln Thr Ser Gln Asp Gly Leu Ser
65                  70                  75                  80

Leu Ala Ser Leu Pro Ser Arg Val Pro Ala Arg Pro Ala Gln Arg Asp
                85                  90                  95

Pro Leu Ser Ser Pro Ala Gly His Thr Val Pro Glu Tyr Arg Asp
            100                 105                 110

Thr Val Ile Phe Asp Asp Pro Arg Leu Val Ser Pro Leu Ser Arg Glu
        115                 120                 125

Val Glu Asp Ala Pro Lys Val Val Glu Pro Ala Ser Glu Arg Glu Gly
    130                 135                 140
```

```
Gly Glu Arg Glu Val Glu Asp Ala Pro Lys Val Val Glu Pro Ala Ser
145                 150                 155                 160

Glu Arg Glu Gly Gly Glu Arg Glu Val Glu Asp Val Pro Lys Val Val
                165                 170                 175

Glu Pro Ala Ser Glu Arg Glu Gly Gly Glu Arg Glu Val Glu Asp Ala
            180                 185                 190

Pro Lys Val Val Glu Pro Ala Ser Glu Arg Glu Gly Gly Glu Arg Glu
        195                 200                 205

Val Glu Asp Val Pro Lys Val Val Glu Pro Ala Ser Glu Arg Glu Gly
    210                 215                 220

Gly Glu Arg Glu Val Glu Asn Val Pro Lys Val Val Glu Pro Ala Ser
225                 230                 235                 240

Glu Arg Glu Gly Gly Glu Arg Glu Val Glu Asp Ala Pro Lys Val Val
                245                 250                 255

Glu Pro Ala Ser Glu Arg Glu Gly Gly Glu Arg Glu Val Glu Asp Ala
            260                 265                 270

Pro Lys Val Val Glu Pro Ala Ser Glu Arg Glu Gly Gly Glu Arg Glu
        275                 280                 285

Val Glu Asp Val Pro Lys Val Val Glu Pro Ala Ser Glu Arg Glu Gly
    290                 295                 300

Gly Glu Arg Glu Val Glu Asp Val Pro Lys Val Val Glu Pro Ala Ser
305                 310                 315                 320

Glu Arg Glu Gly Gly Glu Arg Glu Val Glu Asp Val Pro Lys Val Val
                325                 330                 335

Glu Pro Ala Ser Glu Arg Glu Gly Gly Glu Arg Glu Val Glu Asp Val
            340                 345                 350

Pro Lys Val Val Glu Pro Ala Ser Glu Arg Glu Gly Gly Glu Arg Glu
        355                 360                 365

Val Glu Asp Val Pro Gly Val Val Glu Pro Ala Ser Gly His Glu Gly
    370                 375                 380

Gly Glu Arg Glu Val Glu Asp Val Pro Gly Val Val Glu Pro Ala Ser
385                 390                 395                 400

Gly His Glu Gly Gly Glu Arg Glu Val Ala Ser Gln His Thr Lys Gln
                405                 410                 415

Pro Ser His Ser Val Ser Asn Ser Ala Pro Asn Gln Phe Arg Lys Pro
            420                 425                 430
```

<210> SEQ ID NO 3
<211> LENGTH: 699
<212> TYPE: DNA
<213> ORGANISM: Treponema pallidum
<220> FEATURE:
<221> NAME/KEY: CDS
<222> LOCATION: (1)..(699)
<223> OTHER INFORMATION:
<220> FEATURE:
<221> NAME/KEY: misc_feature
<223> OTHER INFORMATION: Subspecies: pertenue (CDC-2 strain)

<400> SEQUENCE: 3

```
atg ttt gtg cgc agt gac atg ttc ccc aaa aac act gct gtt gaa att    48
Met Phe Val Arg Ser Asp Met Phe Pro Lys Asn Thr Ala Val Glu Ile
1               5                   10                  15 agc aac tta gaa aag aat gcc aag gct cag gca gtg gtt att ggg cac    96
Ser Asn Leu Glu Lys Asn Ala Lys Ala Gln Ala Val Val Ile Gly His
            20                  25                  30 gca ggg atc ccc ggt ctt cta gtt agc ctt gca ccc gct gct gca gca    144
Ala Gly Ile Pro Gly Leu Leu Val Ser Leu Ala Pro Ala Ala Ala Ala
```

```
                35                  40                  45
cag ctt ggg att ggc gta tac caa gct gtg cgt gta cgc gta cgt acc    192
Gln Leu Gly Ile Gly Val Tyr Gln Ala Val Arg Val Arg Val Arg Thr
 50                  55                  60 ttg ggt acc gtg cgc ggt ggg tct caa aca agt cag gac gga ctg tcc    240
Leu Gly Thr Val Arg Gly Gly Ser Gln Thr Ser Gln Asp Gly Leu Ser
 65                  70                  75                  80 ctt gca tct ttg ccg tcc cgt gtg cct gcg cgc ccc gcg cag cgt gat    288
Leu Ala Ser Leu Pro Ser Arg Val Pro Ala Arg Pro Ala Gln Arg Asp
                 85                  90                  95 cct ctg tca tcc ccg ccg gca ggt cac act gta ccg gaa tat cgc gat    336
Pro Leu Ser Ser Pro Pro Ala Gly His Thr Val Pro Glu Tyr Arg Asp
                100                 105                 110 acg gtt att ttc gat gac ccg cgt ttg gtt tcc cct ttg tct cgt gag    384
Thr Val Ile Phe Asp Asp Pro Arg Leu Val Ser Pro Leu Ser Arg Glu
                115                 120                 125 gtg gag gac gtg ccg aag gta gtg gag ccg gcc tct gag cgt gag gga    432
Val Glu Asp Val Pro Lys Val Val Glu Pro Ala Ser Glu Arg Glu Gly
130                 135                 140 ggg gag cgt gag gtg gag gac gtg ccg aag gta gtg gag ccg gcc tct    480
Gly Glu Arg Glu Val Glu Asp Val Pro Lys Val Val Glu Pro Ala Ser
145                 150                 155                 160 gag cgt gag gga ggg gag cgt gag gtg gag gac gtg ccg aag gta gtg    528
Glu Arg Glu Gly Gly Glu Arg Glu Val Glu Asp Val Pro Lys Val Val
                165                 170                 175 gag ccg gcc tct gag cgt gag gga ggg gag cgt gag gtg gag gac gtg    576
Glu Pro Ala Ser Glu Arg Glu Gly Gly Glu Arg Glu Val Glu Asp Val
                180                 185                 190 ccg aag gta gtg gag ccg gcc tct gag cgt gag gga ggg gag cgt gag    624
Pro Lys Val Val Glu Pro Ala Ser Glu Arg Glu Gly Gly Glu Arg Glu
                195                 200                 205 gtc gct tct cag cat acg aag cag cca tcc cac tcg gtt tcc aac tca    672
Val Ala Ser Gln His Thr Lys Gln Pro Ser His Ser Val Ser Asn Ser
210                 215                 220 gct ccc aat cag ttt cgg aaa ccc tga                                699
Ala Pro Asn Gln Phe Arg Lys Pro
225                 230
```

<210> SEQ ID NO 4
<211> LENGTH: 232
<212> TYPE: PRT
<213> ORGANISM: Treponema pallidum
<220> FEATURE:
<221> NAME/KEY: misc_feature
<223> OTHER INFORMATION: Subspecies: pertenue (CDC-2 strain)

<400> SEQUENCE: 4

```
Met Phe Val Arg Ser Asp Met Phe Pro Lys Asn Thr Ala Val Glu Ile
  1               5                  10                  15

Ser Asn Leu Glu Lys Asn Ala Lys Ala Gln Ala Val Val Ile Gly His
                 20                  25                  30

Ala Gly Ile Pro Gly Leu Leu Val Ser Leu Ala Pro Ala Ala Ala
             35                  40                  45

Gln Leu Gly Ile Gly Val Tyr Gln Ala Val Arg Val Arg Val Arg Thr
 50                  55                  60

Leu Gly Thr Val Arg Gly Gly Ser Gln Thr Ser Gln Asp Gly Leu Ser
 65                  70                  75                  80

Leu Ala Ser Leu Pro Ser Arg Val Pro Ala Arg Pro Ala Gln Arg Asp
                 85                  90                  95
```

```
Pro Leu Ser Ser Pro Pro Ala Gly His Thr Val Pro Glu Tyr Arg Asp
            100                 105                 110

Thr Val Ile Phe Asp Asp Pro Arg Leu Val Ser Pro Leu Ser Arg Glu
            115                 120                 125

Val Glu Asp Val Pro Lys Val Val Glu Pro Ala Ser Glu Arg Glu Gly
        130                 135                 140

Gly Glu Arg Glu Val Glu Asp Val Pro Lys Val Val Glu Pro Ala Ser
145                 150                 155                 160

Glu Arg Glu Gly Gly Glu Arg Glu Val Glu Asp Val Pro Lys Val Val
                165                 170                 175

Glu Pro Ala Ser Glu Arg Glu Gly Gly Glu Arg Glu Val Glu Asp Val
            180                 185                 190

Pro Lys Val Val Glu Pro Ala Ser Glu Arg Glu Gly Gly Glu Arg Glu
            195                 200                 205

Val Ala Ser Gln His Thr Lys Gln Pro Ser His Ser Val Ser Asn Ser
        210                 215                 220

Ala Pro Asn Gln Phe Arg Lys Pro
225                 230

<210> SEQ ID NO 5
<211> LENGTH: 939
<212> TYPE: DNA
<213> ORGANISM: Treponema pallidum
<220> FE -continued

```
Gly Glu Arg Glu Val Glu Asp Val Pro Lys Val Val Glu Pro Ala Ser
145                 150                 155                 160 gag cgt gag gga ggg gag cgt gag gtg gag gac gtg ccg aag gta gtg     528
Glu Arg Glu Gly Gly Glu Arg Glu Val Glu Asp Val Pro Lys Val Val
                165                 170                 175 gag ccg gcc tct gag cgt gag gga ggg gag cgt gag gtg gag gac gtg     576
Glu Pro Ala Ser Glu Arg Glu Gly Gly Glu Arg Glu Val Glu Asp Val
            180                 185                 190 ccg aag gta gtg gag ccg gcc tct gag cgt gag gga ggg gag cgt gag     624
Pro Lys Val Val Glu Pro Ala Ser Glu Arg Glu Gly Gly Glu Arg Glu
        195                 200                 205 gtg gag gac gtg ccg aag gta gtg gag ccg gcc tct gag cgt gag gga     672
Val Glu Asp Val Pro Lys Val Val Glu Pro Ala Ser Glu Arg Glu Gly
    210                 215                 220 ggg gag cgt gag gtg gag gac gtg ccg aag gta gtg gag ccg gcc tct     720
Gly Glu Arg Glu Val Glu Asp Val Pro Lys Val Val Glu Pro Ala Ser
225                 230                 235                 240 gag cgt gag gga ggg gag cgt gag gtg gag gac gtg ccg aag gta gtg     768
Glu Arg Glu Gly Gly Glu Arg Glu Val Glu Asp Val Pro Lys Val Val
                245                 250                 255 gag ccg gcc tct gag cgt gag gga ggg gag cgt gag gtg gag gac gtg     816
Glu Pro Ala Ser Glu Arg Glu Gly Gly Glu Arg Glu Val Glu Asp Val
            260                 265                 270 ccg aag gta gtg gag ccg gcc tct gag cgt gag gga ggg gag cgt gag     864
Pro Lys Val Val Glu Pro Ala Ser Glu Arg Glu Gly Gly Glu Arg Glu
        275                 280                 285 gtc gct tct cag cat acg aag cag cca tcc cac tcg gtt tcc aac tca     912
Val Ala Ser Gln His Thr Lys Gln Pro Ser His Ser Val Ser Asn Ser
    290                 295                 300 gct ccc aat cag ttt cgg aaa ccc tga                                 939
Ala Pro Asn Gln Phe Arg Lys Pro
305                 310

<210> SEQ ID NO 6
<211> LENGTH: 312
<212> TYPE: PRT
<213> ORGANISM: Treponema pallidum
<220> FEATURE:
<221> NAME/KEY: misc_feature
<223> OTHER INFORMATION: Subspecies:  endemicum (Bosnia strain)

<400> SEQUENCE: 6

Met Phe Val Arg Ser Asp Met Phe Pro Lys Asn Thr Ala Val Glu Ile
1               5                   10                  15

Ser Asn Leu Glu Lys Asn Ala Lys Ala Gln Ala Val Val Ile Gly His
            20                  25                  30

Ala Gly Ile Pro Gly Leu Leu Val Ser Leu Ala Pro Ala Ala Ala Ala
        35                  40                  45

Gln Leu Gly Ile Gly Val Tyr Gln Ala Val Arg Val Arg Val Arg Thr
    50                  55                  60

Leu Gly Thr Val Arg Gly Gly Ser Gln Thr Ser Gln Asp Gly Leu Ser
65              70                  75                  80

Leu Ala Ser Leu Pro Ser Arg Val Pro Ala Arg Pro Ala Gln Arg Asp
                85                  90                  95

Pro Leu Ser Ser Pro Pro Ala Gly His Thr Val Pro Glu Tyr Arg Asp
            100                 105                 110

Thr Val Ile Phe Asp Asp Pro Arg Leu Val Ser Pro Leu Ser Arg Glu
        115                 120                 125

Val Glu Asp Val Pro Lys Val Val Glu Pro Ala Ser Glu Arg Glu Gly
```

```
                130                 135                 140
Gly Glu Arg Glu Val Glu Asp Val Pro Lys Val Val Glu Pro Ala Ser
145                 150                 155                 160

Glu Arg Glu Gly Gly Glu Arg Glu Val Glu Asp Val Pro Lys Val Val
                165                 170                 175

Glu Pro Ala Ser Glu Arg Glu Gly Gly Glu Arg Glu Val Glu Asp Val
                180                 185                 190

Pro Lys Val Val Glu Pro Ala Ser Glu Arg Glu Gly Gly Glu Arg Glu
                195                 200                 205

Val Glu Asp Val Pro Lys Val Val Glu Pro Ala Ser Glu Arg Glu Gly
210                 215                 220

Gly Glu Arg Glu Val Glu Asp Val Pro Lys Val Val Glu Pro Ala Ser
225                 230                 235                 240

Glu Arg Glu Gly Gly Glu Arg Glu Val Glu Asp Val Pro Lys Val Val
                245                 250                 255

Glu Pro Ala Ser Glu Arg Glu Gly Gly Glu Arg Glu Val Glu Asp Val
                260                 265                 270

Pro Lys Val Val Glu Pro Ala Ser Glu Arg Glu Gly Gly Glu Arg Glu
                275                 280                 285

Val Ala Ser Gln His Thr Lys Gln Pro Ser His Ser Val Ser Asn Ser
290                 295                 300

Ala Pro Asn Gln Phe Arg Lys Pro
305                 310

<210> SEQ ID NO 7
<211> LENGTH: 19
<212> TYPE: PRT
<213> ORGANISM: Treponema pallidum

<400> SEQUENCE: 7

Leu Val Ser Pro Leu Arg Glu Val Glu Asp Ala Pro Lys Val Val Glu
1               5                   10                  15

Pro Ala Ser

<210> SEQ ID NO 8
<211> LENGTH: 20
<212> TYPE: PRT
<213> ORGANISM: Treponema pallidum

<400> SEQUENCE: 8

Ser Arg Glu Val Glu Asp Ala Pro Lys Val Val Glu Pro Ala Ser Glu
1               5                   10                  15

Arg Glu Gly Gly
            20

<210> SEQ ID NO 9
<211> LENGTH: 20
<212> TYPE: PRT
<213> ORGANISM: Treponema pallidum

<400> SEQUENCE: 9

Pro Lys Val Val Glu Pro Ala Ser Glu Arg Glu Gly Gly Glu Arg Glu
1               5                   10                  15

Val Glu Asp Ala
            20

<210> SEQ ID NO 10
<211> LENGTH: 21
```

-continued

<212> TYPE: PRT
<213> ORGANISM: Treponema pallidum

<400> SEQUENCE: 10

Pro Lys Asn Thr Ala Val Glu Ile Ser Asn Leu Glu Lys Asn Ala Lys
1 5 10 15

Ala Gln Ala Val Val
20

<210> SEQ ID NO 11
<211> LENGTH: 25
<212> TYPE: PRT
<213> ORGANISM: Treponema pallidum

<400> SEQUENCE: 11

Gly His Ala Gly Ile Pro Gly Leu Leu Val Ser Leu Ala Pro Ala Ala
1 5 10 15

Ala Ala Gln Leu Gly Ile Gly Val Tyr
20 25

<210> SEQ ID NO 12
<211> LENGTH: 25
<212> TYPE: PRT
<213> ORGANISM: Treponema pallidum

<400> SEQUENCE: 12

Val Pro Ala Arg Pro Ala Gln Arg Asp Pro Leu Ser Ser Pro Pro Ala
1 5 10 15

Gly His Thr Val Pro Glu Tyr Arg Asp
20 25

<210> SEQ ID NO 13
<211> LENGTH: 21
<212> TYPE: PRT
<213> ORGANISM: Treponema pallidum

<400> SEQUENCE: 13

Val Val Glu Pro Ala Ser Glu Arg Glu Gly Gly Glu Arg Glu Val Glu
1 5 10 15

Asp Val Pro Lys Val
20

<210> SEQ ID NO 14
<211> LENGTH: 26
<212> TYPE: PRT
<213> ORGANISM: Treponema pallidum

<400> SEQUENCE: 14

Val Val Glu Pro Ala Ser Gly His Glu Gly Gly Glu Arg Glu Val Ala
1 5 10 15

Ser Gln His Thr Lys Gln Pro Ser His Ser
20 25

<210> SEQ ID NO 15
<211> LENGTH: 20
<212> TYPE: PRT
<213> ORGANISM: Treponema pallidum

<400> SEQUENCE: 15

Glu Val Glu Asp Val Pro Lys Val Val Glu Pro Ala Ser Glu Arg Glu
1 5 10 15

Gly Gly Glu Arg

<210> SEQ ID NO 16
<211> LENGTH: 20
<212> TYPE: PRT
<213> ORGANISM: Treponema pallidum

<400> SEQUENCE: 16

Glu Val Glu Asn Val Pro Lys Val Val Glu Pro Ala Ser Glu Arg Glu
1               5                   10                  15

Gly Gly Glu Arg
            20

<210> SEQ ID NO 17
<211> LENGTH: 20
<212> TYPE: PRT
<213> ORGANISM: Treponema pallidum

<400> SEQUENCE: 17

Glu Val Glu Asp Ala Pro Lys Val Val Glu Pro Ala Ser Glu Arg Glu
1               5                   10                  15

Gly Gly Glu Arg
            20

<210> SEQ ID NO 18
<211> LENGTH: 20
<212> TYPE: PRT
<213> ORGANISM: Treponema pallidum

<400> SEQUENCE: 18

Glu Val Glu Asp Val Pro Gly Val Val Glu Pro Ala Ser Gly His Glu
1               5                   10                  15

Gly Gly Glu Arg
            20

<210> SEQ ID NO 19
<211> LENGTH: 1647
<212> TYPE: DNA
<213> ORGANISM: Treponema pallidum
<220> FEATURE:
<221> NAME/KEY: CDS
<222> LOCATION: (1)..(1647)
<223> OTHER INFORMATION:
<220> FEATURE:
<221> NAME/KEY: misc_feature
<223> OTHER INFORMATION: Subspecies: pallidum (Nichols strain)

<400> SEQUENCE: 19 atg ttt gtg cgc agt gac atg ttc ccc aaa aac act gct gtt gaa att        48
Met Phe Val Arg Ser Asp Met Phe Pro Lys Asn Thr Ala Val Glu Ile
1               5                   10                  15 agc aac tta gaa aag aat gcc aag gct cag gca gtg gtt att ggg cac        96
Ser Asn Leu Glu Lys Asn Ala Lys Ala Gln Ala Val Val Ile Gly His
            20                  25                  30 gca ggg atc ccc ggt ctt cta gtt agc ctt gca ccc gct gct gca gca       144
Ala Gly Ile Pro Gly Leu Leu Val Ser Leu Ala Pro Ala Ala Ala Ala
        35                  40                  45 cag ctt ggg att ggc gta tac caa gct gtg cgt gta cgc gta cgt acc       192
Gln Leu Gly Ile Gly Val Tyr Gln Ala Val Arg Val Arg Val Arg Thr
    50                  55                  60 ttg ggt acc gtg cgc ggt ggg tct caa aca agt cag gac gga ctg tcc       240
Leu Gly Thr Val Arg Gly Gly Ser Gln Thr Ser Gln Asp Gly Leu Ser
65                  70                  75                  80

```
ctt gca tct ttg ccg tcc cgt gtg cct gcg cgc ccc gcg cag cgt gat    288
Leu Ala Ser Leu Pro Ser Arg Val Pro Ala Arg Pro Ala Gln Arg Asp
             85              90              95 cct ctg tca tcc ccg ccg gca ggt cac act gta ccg gaa tat cgc gat    336
Pro Leu Ser Ser Pro Pro Ala Gly His Thr Val Pro Glu Tyr Arg Asp
            100             105             110 acg gtt att ttc gat gac ccg cgt ttg gtt tcc cct ttg tct cgt gag    384
Thr Val Ile Phe Asp Asp Pro Arg Leu Val Ser Pro Leu Ser Arg Glu
        115             120             125 gtg gag gac gcg ccg aag gta gtg gag ccg gcc tct gag cgt gag gga    432
Val Glu Asp Ala Pro Lys Val Val Glu Pro Ala Ser Glu Arg Glu Gly
    130             135             140 ggg gag cgt gag gtg gag gac gcg ccg aag gta gtg gag ccg gcc tct    480
Gly Glu Arg Glu Val Glu Asp Ala Pro Lys Val Val Glu Pro Ala Ser
145             150             155             160 gag cgt gag gga ggg gag cgt gag gtg gag gac gtg ccg aag gta gtg    528
Glu Arg Glu Gly Gly Glu Arg Glu Val Glu Asp Val Pro Lys Val Val
            165             170             175 gag ccg gcc tct gag cgt gag gga ggg gag cgt gag gtg gag gac gcg    576
Glu Pro Ala Ser Glu Arg Glu Gly Gly Glu Arg Glu Val Glu Asp Ala
        180             185             190 ccg aag gta gtg gag ccg gcc tct gag cgt gag gga ggg gag cgt gag    624
Pro Lys Val Val Glu Pro Ala Ser Glu Arg Glu Gly Gly Glu Arg Glu
    195             200             205 gtg gag gac gtg ccg aag gta gtg gag ccg gcc tct gag cgt gag gga    672
Val Glu Asp Val Pro Lys Val Val Glu Pro Ala Ser Glu Arg Glu Gly
    210             215             220 ggg gag cgt gag gtg gag gac gtg ccg aag gta gtg gag ccg gcc tct    720
Gly Glu Arg Glu Val Glu Asp Val Pro Lys Val Val Glu Pro Ala Ser
225             230             235             240 gag cgt gag gga ggg gag cgt gag gtg gag gac gcg ccg aag gta gtg    768
Glu Arg Glu Gly Gly Glu Arg Glu Val Glu Asp Ala Pro Lys Val Val
            245             250             255 gag ccg gcc tct gag cgt gag gga ggg gag cgt gag gtg gag gac gcg    816
Glu Pro Ala Ser Glu Arg Glu Gly Gly Glu Arg Glu Val Glu Asp Ala
        260             265             270 ccg aag gta gtg gag ccg gcc tct gag cgt gag gga ggg gag cgt gag    864
Pro Lys Val Val Glu Pro Ala Ser Glu Arg Glu Gly Gly Glu Arg Glu
    275             280             285 gtg gag gac gtg ccg aag gta gtg gag ccg gcc tct gag cgt gag gga    912
Val Glu Asp Val Pro Lys Val Val Glu Pro Ala Ser Glu Arg Glu Gly
    290             295             300 ggg gag cgt gag gtg gag gac gtg ccg aag gta gtg gag ccg gcc tct    960
Gly Glu Arg Glu Val Glu Asp Val Pro Lys Val Val Glu Pro Ala Ser
305             310             315             320 gag cgt gag gga ggg gag cgt gag gtg gag gac gtg ccg aag gta gtg   1008
Glu Arg Glu Gly Gly Glu Arg Glu Val Glu Asp Val Pro Lys Val Val
            325             330             335 gag ccg gcc tct gag cgt gag gga ggg gag cgt gag gtg gag gac gtg   1056
Glu Pro Ala Ser Glu Arg Glu Gly Gly Glu Arg Glu Val Glu Asp Val
        340             345             350 ccg aag gta gtg gag ccg gcc tct gag cgt gag gga ggg gag cgt gag   1104
Pro Lys Val Val Glu Pro Ala Ser Glu Arg Glu Gly Gly Glu Arg Glu
    355             360             365 gtg gag gac gtg ccg ggg gta gtg gag ccg gcc tct ggg cat gaa gga   1152
Val Glu Asp Val Pro Gly Val Val Glu Pro Ala Ser Gly His Glu Gly
    370             375             380 ggg gag cgt gag gtg gag gac gtg ccg ggg gta gtg gag ccg gcc tct   1200
Gly Glu Arg Glu Val Glu Asp Val Pro Gly Val Val Glu Pro Ala Ser
385             390             395             400
```

-continued

```
ggg cat gaa gga ggg gag cgt gag gtc gct tct cag cat acg aag cag      1248
Gly His Glu Gly Gly Glu Arg Glu Val Ala Ser Gln His Thr Lys Gln
            405                 410                 415 cca tcc cac tcg gtt tcc aac tca gct ccc aat cag ttt cgg aac cct      1296
Pro Ser His Ser Val Ser Asn Ser Ala Pro Asn Gln Phe Arg Asn Pro
        420                 425                 430 gag ggg gaa ctc ccc ttt acg ctc cct gac cta tcc gag tca gaa att      1344
Glu Gly Glu Leu Pro Phe Thr Leu Pro Asp Leu Ser Glu Ser Glu Ile
    435                 440                 445 gtg gtt ccg gag gaa cag aaa gga cgt gcg cat ccc cag gtg ata ccc      1392
Val Val Pro Glu Glu Gln Lys Gly Arg Ala His Pro Gln Val Ile Pro
450                 455                 460 gag ggt gcg cca cgt gga ctg caa cct ggt gaa tac tac gta cag att      1440
Glu Gly Ala Pro Arg Gly Leu Gln Pro Gly Glu Tyr Tyr Val Gln Ile
465                 470                 475                 480 gca gtc ttt cat gac gct atc cag gtg cag agc att gtc cac cgt tac      1488
Ala Val Phe His Asp Ala Ile Gln Val Gln Ser Ile Val His Arg Tyr
                485                 490                 495 ggg gta gaa tac ccc atc gca gtg gag cag gac atc cat gaa ggt aag      1536
Gly Val Glu Tyr Pro Ile Ala Val Glu Gln Asp Ile His Glu Gly Lys
            500                 505                 510 gtg cgt ttc acc gta tgc gtc ggt cct gtc caa aaa gac gaa cgc ggc      1584
Val Arg Phe Thr Val Cys Val Gly Pro Val Gln Lys Asp Glu Arg Gly
        515                 520                 525 gcg gta cta gag aac ttc caa agg ttt gga ttc aag gac gcc ttt ctg      1632
Ala Val Leu Glu Asn Phe Gln Arg Phe Gly Phe Lys Asp Ala Phe Leu
    530                 535                 540 aaa aag gcg cga tga                                                  1647
Lys Lys Ala Arg
545
```

<210> SEQ ID NO 20
<211> LENGTH: 548
<212> TYPE: PRT
<213> ORGANISM: Treponema pallidum
<220> FEATURE:
<221> NAME/KEY: misc_feature
<223> OTHER INFORMATION: Subspecies: pallidum (Nichols strain)

<400> SEQUENCE: 20

```
Met Phe Val Arg Ser Asp Met Phe Pro Lys Asn Thr Ala Val Glu Ile
1               5                   10                  15

Ser Asn Leu Glu Lys Asn Ala Lys Ala Gln Ala Val Val Ile Gly His
            20                  25                  30

Ala Gly Ile Pro Gly Leu Leu Val Ser Leu Ala Pro Ala Ala Ala
        35                  40                  45

Gln Leu Gly Ile Gly Val Tyr Gln Ala Val Arg Val Arg Val Arg Thr
    50                  55                  60

Leu Gly Thr Val Arg Gly Gly Ser Gln Thr Ser Gln Asp Gly Leu Ser
65                  70                  75                  80

Leu Ala Ser Leu Pro Ser Arg Val Pro Ala Arg Pro Ala Gln Arg Asp
                85                  90                  95

Pro Leu Ser Ser Pro Ala Gly His Thr Val Pro Glu Tyr Arg Asp
            100                 105                 110

Thr Val Ile Phe Asp Asp Pro Arg Leu Val Ser Pro Leu Ser Arg Glu
        115                 120                 125

Val Glu Asp Ala Pro Lys Val Val Glu Pro Ala Ser Glu Arg Glu Gly
    130                 135                 140
```

```
Gly Glu Arg Glu Val Glu Asp Ala Pro Lys Val Val Glu Pro Ala Ser
145                 150                 155                 160

Glu Arg Glu Gly Gly Glu Arg Glu Val Glu Asp Val Pro Lys Val Val
            165                 170                 175

Glu Pro Ala Ser Glu Arg Glu Gly Gly Glu Arg Glu Val Glu Asp Ala
            180                 185                 190

Pro Lys Val Val Glu Pro Ala Ser Glu Arg Glu Gly Gly Glu Arg Glu
        195                 200                 205

Val Glu Asp Val Pro Lys Val Val Glu Pro Ala Ser Glu Arg Glu Gly
    210                 215                 220

Gly Glu Arg Glu Val Glu Asp Val Pro Lys Val Val Glu Pro Ala Ser
225                 230                 235                 240

Glu Arg Glu Gly Gly Glu Arg Glu Val Glu Asp Ala Pro Lys Val Val
            245                 250                 255

Glu Pro Ala Ser Glu Arg Glu Gly Gly Glu Arg Glu Val Glu Asp Ala
            260                 265                 270

Pro Lys Val Val Glu Pro Ala Ser Glu Arg Glu Gly Gly Glu Arg Glu
        275                 280                 285

Val Glu Asp Val Pro Lys Val Val Glu Pro Ala Ser Glu Arg Glu Gly
    290                 295                 300

Gly Glu Arg Glu Val Glu Asp Val Pro Lys Val Val Glu Pro Ala Ser
305                 310                 315                 320

Glu Arg Glu Gly Gly Glu Arg Glu Val Glu Asp Val Pro Lys Val Val
            325                 330                 335

Glu Pro Ala Ser Glu Arg Glu Gly Gly Glu Arg Glu Val Glu Asp Val
            340                 345                 350

Pro Lys Val Val Glu Pro Ala Ser Glu Arg Glu Gly Gly Glu Arg Glu
        355                 360                 365

Val Glu Asp Val Pro Gly Val Val Glu Pro Ala Ser Gly His Glu Gly
    370                 375                 380

Gly Glu Arg Glu Val Glu Asp Val Pro Gly Val Val Glu Pro Ala Ser
385                 390                 395                 400

Gly His Glu Gly Gly Glu Arg Glu Val Ala Ser Gln His Thr Lys Gln
            405                 410                 415

Pro Ser His Ser Val Ser Asn Ser Ala Pro Asn Gln Phe Arg Asn Pro
            420                 425                 430

Glu Gly Glu Leu Pro Phe Thr Leu Pro Asp Leu Ser Glu Ser Glu Ile
            435                 440                 445

Val Val Pro Glu Glu Gln Lys Gly Arg Ala His Pro Gln Val Ile Pro
        450                 455                 460

Glu Gly Ala Pro Arg Gly Leu Gln Pro Gly Glu Tyr Tyr Val Gln Ile
465                 470                 475                 480

Ala Val Phe His Asp Ala Ile Gln Val Gln Ser Ile Val His Arg Tyr
            485                 490                 495

Gly Val Glu Tyr Pro Ile Ala Val Glu Gln Asp Ile His Glu Gly Lys
            500                 505                 510

Val Arg Phe Thr Val Cys Val Gly Pro Val Gln Lys Asp Glu Arg Gly
            515                 520                 525

Ala Val Leu Glu Asn Phe Gln Arg Phe Gly Lys Asp Ala Phe Leu
530                 535                 540

Lys Lys Ala Arg
545
```

<210> SEQ ID NO 21
<211> LENGTH: 1047
<212> TYPE: DNA
<213> ORGANISM: Treponema pallidum
<220> FEATURE:
<221> NAME/KEY: CDS
<222> LOCATION: (1)..(1047)
<223> OTHER INFORMATION:
<220> FEATURE:
<221> NAME/KEY: misc_feature
<223> OTHER INFORMATION: Subspecies: perten -continued

```
Arg Ala His Pro Gln Val Ile Pro Glu Gly Ala Pro Arg Gly Leu Gln
                260                 265                 270 cct ggt gaa tac tac gta cag att gca gtc ttt cat gac gct atc cag    864
Pro Gly Glu Tyr Tyr Val Gln Ile Ala Val Phe His Asp Ala Ile Gln
            275                 280                 285 gtg cag agc att gtc cac cgt tac ggg gta gaa tac ccc atc gca gtg    912
Val Gln Ser Ile Val His Arg Tyr Gly Val Glu Tyr Pro Ile Ala Val
        290                 295                 300 gag cag gac atc cat gaa ggt aag gtg cgt ttc acc gta tgc gtc ggt    960
Glu Gln Asp Ile His Glu Gly Lys Val Arg Phe Thr Val Cys Val Gly
305                 310                 315                 320 cct gtc caa aaa gac gaa cgc ggc gcg gta cta gag aac ttc caa agg   1008
Pro Val Gln Lys Asp Glu Arg Gly Ala Val Leu Glu Asn Phe Gln Arg
                325                 330                 335 ttt gga ttc aag gac gcc ttt ctg aaa aag gcg cga tga                1047
Phe Gly Phe Lys Asp Ala Phe Leu Lys Lys Ala Arg
            340                 345
```

<210> SEQ ID NO 22
<211> LENGTH: 348
<212> TYPE: PRT
<213> ORGANISM: Treponema pallidum
<220> FEATURE:
<221> NAME/KEY: misc_feature
<223> OTHER INFORMATION: Subspecies: pertenue (CDC-2 strain)

<400> SEQUENCE: 22

```
Met Phe Val Arg Ser Asp Met Phe Pro Lys Asn Thr Ala Val Glu Ile
1               5                   10                  15

Ser Asn Leu Glu Lys Asn Ala Lys Ala Gln Ala Val Val Ile Gly His
                20                  25                  30

Ala Gly Ile Pro Gly Leu Leu Val Ser Leu Ala Pro Ala Ala Ala Ala
            35                  40                  45

Gln Leu Gly Ile Gly Val Tyr Gln Ala Val Arg Val Arg Val Arg Thr
        50                  55                  60

Leu Gly Thr Val Arg Gly Gly Ser Gln Thr Ser Gln Asp Gly Leu Ser
65                  70                  75                  80

Leu Ala Ser Leu Pro Ser Arg Val Pro Ala Arg Pro Ala Gln Arg Asp
                85                  90                  95

Pro Leu Ser Ser Pro Pro Ala Gly His Thr Val Pro Glu Tyr Arg Asp
            100                 105                 110

Thr Val Ile Phe Asp Asp Pro Arg Leu Val Ser Pro Leu Ser Arg Glu
        115                 120                 125

Val Glu Asp Val Pro Lys Val Val Glu Pro Ala Ser Glu Arg Glu Gly
    130                 135                 140

Gly Glu Arg Glu Val Glu Asp Val Pro Lys Val Val Glu Pro Ala Ser
145                 150                 155                 160

Glu Arg Glu Gly Gly Glu Arg Glu Val Glu Asp Val Pro Lys Val Val
                165                 170                 175

Glu Pro Ala Ser Glu Arg Glu Gly Gly Glu Arg Glu Val Glu Asp Val
            180                 185                 190

Pro Lys Val Val Glu Pro Ala Ser Glu Arg Glu Gly Gly Glu Arg Glu
        195                 200                 205

Val Ala Ser Gln His Thr Lys Gln Pro Ser His Ser Val Ser Asn Ser
    210                 215                 220

Ala Pro Asn Gln Phe Arg Asn Pro Glu Gly Glu Leu Pro Phe Thr Leu
225                 230                 235                 240
```

-continued

```
Pro Asp Leu Ser Glu Ser Glu Ile Val Val Pro Glu Gln Lys Gly
            245                 250                 255

Arg Ala His Pro Gln Val Ile Pro Glu Gly Ala Pro Arg Gly Leu Gln
            260                 265                 270

Pro Gly Glu Tyr Tyr Val Gln Ile Ala Val Phe His Asp Ala Ile Gln
            275                 280                 285

Val Gln Ser Ile Val His Arg Tyr Gly Val Glu Tyr Pro Ile Ala Val
        290                 295                 300

Glu Gln Asp Ile His Glu Gly Lys Val Arg Phe Thr Val Cys Val Gly
305                 310                 315                 320

Pro Val Gln Lys Asp Glu Arg Gly Ala Val Leu Glu Asn Phe Gln Arg
                325                 330                 335

Phe Gly Phe Lys Asp Ala Phe Leu Lys Lys Ala Arg
            340                 345
```

<210> SEQ ID NO 23
<211> LENGTH: 1287
<212> TYPE: DNA
<213> ORGANISM: Treponema pallidum
<220> FEATURE:
<221> NAME/KEY: CDS
<222> LOCATION: (1)..(1287)
<223> OTHER INFORMATION:
<220> FEATURE:
<221> NAME/KEY: misc_feature
<223> OTHER INFORMATION: Subspecies: endemicum (Bosnia strain)

<400> SEQUENCE: 23

```
atg ttt gtg cgc agt gac atg ttc ccc aaa aac act gct gtt gaa att    48
Met Phe Val Arg Ser Asp Met Phe Pro Lys Asn Thr Ala Val Glu Ile
1               5                   10                  15 agc aac tta gaa aag aat gcc aag gct cag gca

| | | |
|---|---|---|
| gag ccg gcc tct gag cgt gag gga ggg gag cgt gag gtg gag gac gtg<br>Glu Pro Ala Ser Glu Arg Glu Gly Gly Glu Arg Glu Val Glu Asp Val<br>180 185 190 | | 576 |
| ccg aag gta gtg gag ccg gcc tct gag cgt gag gga ggg gag cgt gag<br>Pro Lys Val Val Glu Pro Ala Ser Glu Arg Glu Gly Gly Glu Arg Glu<br>195 200 205 | | 624 |
| gtg gag gac gtg ccg aag gta gtg gag ccg gcc tct gag cgt gag gga<br>Val Glu Asp Val Pro Lys Val Val Glu Pro Ala Ser Glu Arg Glu Gly<br>210 215 220 | | 672 |
| ggg gag cgt gag gtg gag gac gtg ccg aag gta gtg gag ccg gcc tct<br>Gly Glu Arg Glu Val Glu Asp Val Pro Lys Val Val Glu Pro Ala Ser<br>225 230 235 240 | | 720 |
| gag cgt gag gga ggg gag cgt gag gtg gag gac gtg ccg aag gta gtg<br>Glu Arg Glu Gly Gly Glu Arg Glu Val Glu Asp Val Pro Lys Val Val<br>245 250 255 | | 768 |
| gag ccg gcc tct gag cgt gag gga ggg gag cgt gag gtg gag gac gtg<br>Glu Pro Ala Ser Glu Arg Glu Gly Gly Glu Arg Glu Val Glu Asp Val<br>260 265 270 | | 816 |
| ccg aag gta gtg gag ccg gcc tct gag cgt gag gga ggg gag cgt gag<br>Pro Lys Val Val Glu Pro Ala Ser Glu Arg Glu Gly Gly Glu Arg Glu<br>275 280 285 | | 864 |
| gtc gct tct cag cat acg aag cag cca tcc cac tcg gtt tcc aac tca<br>Val Ala Ser Gln His Thr Lys Gln Pro Ser His Ser Val Ser Asn Ser<br>290 295 300 | | 912 |
| gct ccc aat cag ttt cgg aac cct gag ggg gaa ctc ccc ttt acg ctc<br>Ala Pro Asn Gln Phe Arg Asn Pro Glu Gly Glu Leu Pro Phe Thr Leu<br>305 310 315 320 | | 960 |
| cct gac cta tcc gag tca gaa att gtg gtt ccg gag gaa cag aaa gga<br>Pro Asp Leu Ser Glu Ser Glu Ile Val Val Pro Glu Glu Gln Lys Gly<br>325 330 335 | | 1008 |
| cgt gcg cat ccc cag gtg ata ccc gag ggt gcg cca cgt gga ctg caa<br>Arg Ala His Pro Gln Val Ile Pro Glu Gly Ala Pro Arg Gly Leu Gln<br>340 345 350 | | 1056 |
| cct ggt gaa tac tac gta cag att gca gtc ttt cat gac gct atc cag<br>Pro Gly Glu Tyr Tyr Val Gln Ile Ala Val Phe His Asp Ala Ile Gln<br>355 360 365 | | 1104 |
| gtg cag agc att gtc cac cgt tac ggg gta gaa tac ccc atc gca gtg<br>Val Gln Ser Ile Val His Arg Tyr Gly Val Glu Tyr Pro Ile Ala Val<br>370 375 380 | | 1152 |
| gag cag gac atc cat gaa ggt aag gtg cgt ttc acc gta tgc gtc ggt<br>Glu Gln Asp Ile His Glu Gly Lys Val Arg Phe Thr Val Cys Val Gly<br>385 390 395 400 | | 1200 |
| cct gtc caa aaa gac gaa cgc ggc gcg gta cta gag aac ttc caa agg<br>Pro Val Gln Lys Asp Glu Arg Gly Ala Val Leu Glu Asn Phe Gln Arg<br>405 410 415 | | 1248 |
| ttt gga ttc aag gac gcc ttt ctg aaa aag gcg cga tga<br>Phe Gly Phe Lys Asp Ala Phe Leu Lys Lys Ala Arg<br>420 425 | | 1287 |

<210> SEQ ID NO 24
<211> LENGTH: 428
<212> TYPE: PRT
<213> ORGANISM: Treponema pallidum
<220> FEATURE:
<221> NAME/KEY: misc_feature
<223> OTHER INFORMATION: Subspecies: endemicum (Bosnia strain)

<400> SEQUENCE: 24

Met Phe Val Arg Ser Asp Met Phe Pro Lys Asn Thr Ala Val Glu Ile
1               5                   10                  15

```
Ser Asn Leu Glu Lys Asn Ala Lys Ala Gln Ala Val Val Ile Gly His
            20                  25                  30

Ala Gly Ile Pro Gly Leu Leu Val Ser Leu Ala Pro Ala Ala Ala Ala
        35                  40                  45

Gln Leu Gly Ile Gly Val Tyr Gln Ala Val Arg Val Arg Val Arg Thr
    50                  55                  60

Leu Gly Thr Val Arg Gly Gly Ser Gln Thr Ser Gln Asp Gly Leu Ser
65                  70                  75                  80

Leu Ala Ser Leu Pro Ser Arg Val Pro Ala Arg Pro Ala Gln Arg Asp
                85                  90                  95

Pro Leu Ser Ser Pro Pro Ala Gly His Thr Val Pro Glu Tyr Arg Asp
            100                 105                 110

Thr Val Ile Phe Asp Asp Pro Arg Leu Val Ser Pro Leu Ser Arg Glu
        115                 120                 125

Val Glu Asp Val Pro Lys Val Val Glu Pro Ala Ser Glu Arg Glu Gly
    130                 135                 140

Gly Glu Arg Glu Val Glu Asp Val Pro Lys Val Val Glu Pro Ala Ser
145                 150                 155                 160

Glu Arg Glu Gly Gly Glu Arg Glu Val Glu Asp Val Pro Lys Val Val
                165                 170                 175

Glu Pro Ala Ser Glu Arg Glu Gly Gly Glu Arg Glu Val Glu Asp Val
            180                 185                 190

Pro Lys Val Val Glu Pro Ala Ser Glu Arg Glu Gly Gly Glu Arg Glu
        195                 200                 205

Val Glu Asp Val Pro Lys Val Val Glu Pro Ala Ser Glu Arg Glu Gly
    210                 215                 220

Gly Glu Arg Glu Val Glu Asp Val Pro Lys Val Val Glu Pro Ala Ser
225                 230                 235                 240

Glu Arg Glu Gly Gly Glu Arg Glu Val Glu Asp Val Pro Lys Val Val
                245                 250                 255

Glu Pro Ala Ser Glu Arg Glu Gly Gly Glu Arg Glu Val Glu Asp Val
            260                 265                 270

Pro Lys Val Val Glu Pro Ala Ser Glu Arg Glu Gly Gly Glu Arg Glu
        275                 280                 285

Val Ala Ser Gln His Thr Lys Gln Pro Ser His Ser Val Ser Asn Ser
    290                 295                 300

Ala Pro Asn Gln Phe Arg Asn Pro Glu Gly Glu Leu Pro Phe Thr Leu
305                 310                 315                 320

Pro Asp Leu Ser Glu Ser Glu Ile Val Val Pro Glu Gln Lys Gly
                325                 330                 335

Arg Ala His Pro Gln Val Ile Pro Glu Gly Ala Pro Arg Gly Leu Gln
            340                 345                 350

Pro Gly Glu Tyr Tyr Val Gln Ile Ala Val Phe His Asp Ala Ile Gln
        355                 360                 365

Val Gln Ser Ile Val His Arg Tyr Gly Val Glu Tyr Pro Ile Ala Val
    370                 375                 380

Glu Gln Asp Ile His Glu Gly Lys Val Arg Phe Thr Val Cys Val Gly
385                 390                 395                 400

Pro Val Gln Lys Asp Glu Arg Gly Ala Val Leu Glu Asn Phe Gln Arg
                405                 410                 415

Phe Gly Phe Lys Asp Ala Phe Leu Lys Lys Ala Arg
            420                 425
```

<210> SEQ ID NO 25
<211> LENGTH: 1182
<212> TYPE: DNA
<213> ORGANISM: Treponema pallidum
<220> FEATURE:
<221> NAME/KEY: CDS
<222> LOCATION: (1)..(1182)
<223> OTHER INFORMATION:
<220> FEATURE:
<221> NAME/KEY: misc_feature
<223> OTHER INFORMATION: Subspecies: pertenue (CDC-1 strain)

<400> SEQUENCE: 25

| | | |
|---|---|---|
| atg ttt gtg cgc agt gac atg ttc ccc aaa aac act gct gtt gaa att<br>Met Phe Val Arg Ser Asp Met Phe Pro Lys Asn Thr Ala Val Glu Ile<br>1                  5                    10                15 | | 48 |
| agc aac tta gaa aag aat gcc aag gct cag gca gtg gtt att ggg cac<br>Ser Asn Leu Glu Lys Asn Ala Lys Ala Gln Ala Val Val Ile Gly His<br>                   20                    25                    30 | | 96 |
| gca ggg atc ccc ggt ctt cta gtt agc ctt gca ccc gct gct gca gca<br>Ala Gly Ile Pro Gly Leu Leu Val Ser Leu Ala Pro Ala Ala Ala Ala<br>                   35                    40                    45 | | 144 |
| cag ctt ggg att ggc gta tac caa gct gtg cgt gta cgc gta cgt acc<br>Gln Leu Gly Ile Gly Val Tyr Gln Ala Val Arg Val Arg Val Arg Thr<br>50                    55                    60 | | 192 |
| ttg ggt acc gtg cgc ggt ggg tct caa aca agt cag gac gga ctg tcc<br>Leu Gly Thr Val Arg Gly Gly Ser Gln Thr Ser Gln Asp Gly Leu Ser<br>65                    70                    75                    80 | | 240 |
| ctt gca tct ttg ccg tcc cgt gtg cct gcg cgc ccc gcg cag cgt gat<br>Leu Ala Ser Leu Pro Ser Arg Val Pro Ala Arg Pro Ala Gln Arg Asp<br>                   85                    90                    95 | | 288 |
| cct ctg tca tcc ccg ccg gca ggt cac act gta ccg gaa tat cgc gat<br>Pro Leu Ser Ser Pro Pro Ala Gly His Thr Val Pro Glu Tyr Arg Asp<br>                 100                 105                110 | | 336 |
| acg gtt att ttc gat gac ccg cgt ttg gtt tcc cct ttg tct cgt gag<br>Thr Val Ile Phe Asp Asp Pro Arg Leu Val Ser Pro Leu Ser Arg Glu<br>               115                 120                125 | | 384 |
| gga ggg gag cgt gag gtg gag gac gtg ccg aag gta gtg gag ccg gcc<br>Gly Gly Glu Arg Glu Val Glu Asp Val Pro Lys Val Val Glu Pro Ala<br>130                   135                   140 | | 432 |
| tct gag cgt gag gga ggg gag cgt gag gtg gag gac gtg ccg aag gta<br>Ser Glu Arg Glu Gly Gly Glu Arg Glu Val Glu Asp Val Pro Lys Val<br>145                   150                   155                160 | | 480 |
| gtg gag ccg gcc tct gag cgt gag gga ggg gag cgt gag gtg gag gac<br>Val Glu Pro Ala Ser Glu Arg Glu Gly Gly Glu Arg Glu Val Glu Asp<br>                   165                 170                175 | | 528 |
| gtg ccg aag gta gtg gag ccg gcc tct gag cgt gag gga ggg gag cgt<br>Val Pro Lys Val Val Glu Pro Ala Ser Glu Arg Glu Gly Gly Glu Arg<br>               180                 185                190 | | 576 |
| gag gtg gag gac gtg ccg aag gta gtg gag ccg gcc tct gag cgt gag<br>Glu Val Glu Asp Val Pro Lys Val Val Glu Pro Ala Ser Glu Arg Glu<br>               195                 200                205 | | 624 |
| gga ggg gag cgt gag gtg gag gac gtg ccg aag gta gtg gag ccg gcc<br>Gly Gly Glu Arg Glu Val Glu Asp Val Pro Lys Val Val Glu Pro Ala<br>210                   215                   220 | | 672 |
| tct gag cgt gag gga ggg gag cgt gag gtg gag gac gtg ccg aag gta<br>Ser Glu Arg Glu Gly Gly Glu Arg Glu Val Glu Asp Val Pro Lys Val<br>225                   230                   235                240 | | 720 |
| gtg gag ccg gcc tct gag cgt gag gga ggg gag cgt gag gtc gct tct<br>Val Glu Pro Ala Ser Glu Arg Glu Gly Gly Glu Arg Glu Val Ala Ser<br>                   245                 250                255 | | 768 |
| cag cat acg aag cag cca tcc cac tcg gtt tcc aac tca gct ccc aat | | 816 |

-continued

```
                Gln His Thr Lys Gln Pro Ser His Ser Val Ser Asn Ser Ala Pro Asn
                                260                 265                 270 cag ttt cgg aac cct gag ggg gaa ctc ccc ttt acg ctc cct gac cta                864
Gln Phe Arg Asn Pro Glu Gly Glu Leu Pro Phe Thr Leu Pro Asp Leu
            275                 280                 285 tcc gag tca gaa att gtg gtt ccg gag gaa cag aaa gga cgt gcg cat                912
Ser Glu Ser Glu Ile Val Val Pro Glu Glu Gln Lys Gly Arg Ala His
290                 295                 300 ccc cag gtg ata ccc gag ggt gcg cca cgt gga ctg caa cct ggt gaa                960
Pro Gln Val Ile Pro Glu Gly Ala Pro Arg Gly Leu Gln Pro Gly Glu
305                 310                 315                 320 tac tac gta cag att gca gtc ttt cat gac gct atc cag gtg cag agc               1008
Tyr Tyr Val Gln Ile Ala Val Phe His Asp Ala Ile Gln Val Gln Ser
                325                 330                 335 att gtc cac cgt tac ggg gta gaa tac ccc atc gca gtg gag cag gac               1056
Ile Val His Arg Tyr Gly Val Glu Tyr Pro Ile Ala Val Glu Gln Asp
            340                 345                 350 atc cat gaa ggt aag gtg cgt ttc acc gta tgc gtc ggt cct gtc caa               1104
Ile His Glu Gly Lys Val Arg Phe Thr Val Cys Val Gly Pro Val Gln
355                 360                 365 aaa gac gaa cgc ggc gcg gta cta gag aac ttc caa agg ttt gga ttc               1152
Lys Asp Glu Arg Gly Ala Val Leu Glu Asn Phe Gln Arg Phe Gly Phe
370                 375                 380 aag gac gcc ttt ctg aaa aag gcg cga tga                                        1182
Lys Asp Ala Phe Leu Lys Lys Ala Arg
385                 390

<210> SEQ ID NO 26
<211> LENGTH: 393
<212> TYPE: PRT
<213> ORGANISM: Treponema pallidum
<220> FEATURE:
<221> NAME/KEY: misc_feature
<223> OTHER INFORMATION: Subspecies: pertenue (CDC-1 strain)

<400> SEQUENCE: 26

Met Phe Val Arg Ser Asp Met Phe Pro Lys Asn Thr Ala Val Glu Ile
1               5                   10                  15

Ser Asn Leu Glu Lys Asn Ala Lys Ala Gln Ala Val Val Ile Gly His
                20                  25                  30

Ala Gly Ile Pro Gly Leu Leu Val Ser Leu Ala Pro Ala Ala Ala Ala
            35                  40                  45

Gln Leu Gly Ile Gly Val Tyr Gln Ala Val Arg Val Arg Val Arg Thr
        50                  55                  60

Leu Gly Thr Val Arg Gly Gly Ser Gln Thr Ser Gln Asp Gly Leu Ser
65                  70                  75                  80

Leu Ala Ser Leu Pro Ser Arg Val Pro Ala Arg Pro Ala Gln Arg Asp
                85                  90                  95

Pro Leu Ser Ser Pro Ala Gly His Thr Val Pro Glu Tyr Arg Asp
            100                 105                 110

Thr Val Ile Phe Asp Asp Pro Arg Leu Val Ser Pro Leu Ser Arg Glu
        115                 120                 125

Gly Gly Glu Arg Glu Val Glu Asp Val Pro Lys Val Val Glu Pro Ala
130                 135                 140

Ser Glu Arg Glu Gly Gly Glu Arg Glu Val Glu Asp Val Pro Lys Val
145                 150                 155                 160

Val Glu Pro Ala Ser Glu Arg Glu Gly Gly Glu Arg Glu Val Glu Asp
                165                 170                 175
```

-continued

```
Val Pro Lys Val Val Glu Pro Ala Ser Glu Arg Glu Gly Gly Glu Arg
            180                 185                 190

Glu Val Glu Asp Val Pro Lys Val Val Glu Pro Ala Ser Glu Arg Glu
            195                 200                 205

Gly Gly Glu Arg Glu Val Glu Asp Val Pro Lys Val Val Glu Pro Ala
    210                 215                 220

Ser Glu Arg Glu Gly Gly Glu Arg Glu Val Glu Asp Val Pro Lys Val
225                 230                 235                 240

Val Glu Pro Ala Ser Glu Arg Glu Gly Gly Glu Arg Glu Val Ala Ser
                245                 250                 255

Gln His Thr Lys Gln Pro Ser His Ser Val Ser Asn Ser Ala Pro Asn
                260                 265                 270

Gln Phe Arg Asn Pro Glu Gly Glu Leu Pro Phe Thr Leu Pro Asp Leu
            275                 280                 285

Ser Glu Ser Glu Ile Val Val Pro Glu Glu Gln Lys Gly Arg Ala His
    290                 295                 300

Pro Gln Val Ile Pro Glu Gly Ala Pro Arg Gly Leu Gln Pro Gly Glu
305                 310                 315                 320

Tyr Tyr Val Gln Ile Ala Val Phe His Asp Ala Ile Gln Val Gln Ser
                325                 330                 335

Ile Val His Arg Tyr Gly Val Glu Tyr Pro Ile Ala Val Glu Gln Asp
            340                 345                 350

Ile His Glu Gly Lys Val Arg Phe Thr Val Cys Val Gly Pro Val Gln
            355                 360                 365

Lys Asp Glu Arg Gly Ala Val Leu Glu Asn Phe Gln Arg Phe Gly Phe
            370                 375                 380

Lys Asp Ala Phe Leu Lys Lys Ala Arg
385                 390
```